(12) United States Patent
Waer et al.

(10) Patent No.: US 7,276,506 B2
(45) Date of Patent: Oct. 2, 2007

(54) IMMUNOSUPPRESSIVE EFFECTS OF PTERIDINE DERIVATIVES

(75) Inventors: Mark Jozef Albert Waer, Heverlee (BE); Piet André Maurits Maria Herdewijn, Rotselaar/Wezemaal (BE); Wolfgang Eugen Pfleiderer, Constance (DE)

(73) Assignee: 4 Aza Bioscience NV, Leuven (BE)

( * ) Notice: Subject to any disclaimer, the term of this patent is extended or adjusted under 35 U.S.C. 154(b) by 93 days.

(21) Appl. No.: 10/651,604

(22) Filed: Aug. 29, 2003

(65) Prior Publication Data

US 2004/0077859 A1    Apr. 22, 2004

Related U.S. Application Data

(63) Continuation-in-part of application No. 09/869,468, filed as application No. PCT/EP99/10320 on Dec. 28, 1999, now abandoned.

(60) Provisional application No. 60/113,989, filed on Dec. 28, 1998.

(51) Int. Cl.
C07D 475/04    (2006.01)
A61K 31/4985    (2006.01)

(52) U.S. Cl. ..................... 514/249; 544/258

(58) Field of Classification Search ............... 514/249; 544/258, 259, 260
See application file for complete search history.

(56) References Cited

U.S. PATENT DOCUMENTS

| | | | |
|---|---|---|---|
| 2,512,572 A | 6/1950 | Smith, Jr. et al. | |
| 2,581,889 A | 1/1952 | Timmis | |
| 2,665,275 A | 1/1954 | Campbell et al. | |
| 2,667,486 A | 1/1954 | Cain | |
| 2,740,784 A | 4/1956 | Sletzinger et al. | |
| 2,940,972 A | 6/1960 | Roch | |
| 3,081,230 A | 3/1963 | Weinstock et al. | |
| 3,475,425 A * | 10/1969 | Roch ........................... | 544/81 |
| 5,047,405 A | 9/1991 | Gennari | |
| 5,665,772 A | 9/1997 | Cottens et al. | |
| 5,780,462 A | 7/1998 | Lee et al. | |
| 5,929,046 A | 7/1999 | McMurry et al. | |
| 5,992,713 A | 11/1999 | Manabat | |
| 6,331,547 B1 | 12/2001 | Zhu et al. | |
| 6,440,991 B1 | 8/2002 | Zhu et al. | |
| 6,844,343 B1 * | 1/2005 | Pfleiderer et al. ............ | 514/249 |

FOREIGN PATENT DOCUMENTS

| | | |
|---|---|---|
| CH | 231852 | 7/1944 |
| EP | 0 108 890 B | 5/1984 |
| EP | 0 290 819 B | 11/1988 |
| EP | 0 362 645 B | 4/1990 |
| EP | 0 956 855 B | 11/1999 |
| EP | 1 479 682 B | 11/2004 |
| GB | 677342 | 8/1952 |
| GB | 763044 | 12/1956 |
| GB | 785353 | 10/1957 |
| GB | 2405793 A1 * | 3/2005 |
| WO | WO95/31987 | 11/1995 |
| WO | WO95/32203 | 11/1995 |
| WO | WO98/04558 | 2/1998 |
| WO | WO98/08516 | 3/1998 |
| WO | WO 00/39129 | 7/2000 |
| WO | WO 01/19825 | 3/2001 |
| WO | WO 2001021619 A1 * | 3/2005 |

OTHER PUBLICATIONS

West, Anthony R., Solid State Chemistry and its Applications, Wiley, New York, 1988, pp. 358 & 365.*
Mitchell S. Cairo, M.D, "Immunology Lecture #20 Transplantation", Columbia University, [online] Sep. 30, 2003, [retrieved on Jul. 12, 2005]. Retrieved from the internet, <http://healthsciences.columbia.edu/dept/ps/2007/immuno/2006/IM20.pdf>.*
Gabor G Illei, and Peter E Lipsky, Current Opinion in Immunology Vol. 12, Issue 6, Dec. 1, 2000, pp. 712-718.*
Black, Roy A. et al, Ann. Rep. Med. Chem., 32, 1997, 241-250.*
Chantry, D., Emerging Drugs, 1999, Chapter 1, pp. 5-13.*
Froehlich, Lothar G.; Kotsonis, Peter; Traub, Hermann; Taghavi-Moghadam, Shahriyar; Al-Masoudi, Najim; Hofmann, Heinrich; Strobel, Hartmut; Matter, Hans; Pfleiderer, Wolfgang; Schmidt, Harald H. H. W. Journal of Medicinal Chemistry, 42(20), 4108-4131 (English) 1999.*

(Continued)

Primary Examiner—Deepak Rao
(74) Attorney, Agent, or Firm—Clark & Elbing LLP

(57) ABSTRACT

This invention relates to a group of trisubstituted and tetrasubstituted pteridine derivatives, having the formula:

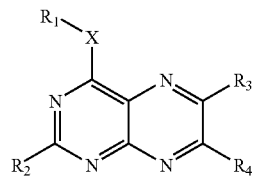

wherein X represents an oxygen atom or a group with the formula NZ and wherein: $R_1$ $C_{1-7}$ alkyl or arylalkyl; Z is a group independently defined as $R_1$ or the group NZ together with $R_1$ is an optionally substituted heterocyclic group containing at least one nitrogen atom; $R_2$ is amino or acylamino; $R_4$ is an atom or a group selected from the group consisting of hydrogen; $C_{1-7}$ alkyl; and $C_{1-7}$ alkoxy; and $R_3$ is an atom or a group selected from the group consisting of aryl optionally substituted with one or more substituents selected from the group consisting of halogen, $C_{1-7}$ alkyl, and $C_{1-7}$ alkoxy, their pharmaceutically acceptable salts, and enantiomers, possessing unexpectedly desirable pharmaceutical properties, in particular which are highly active immunosuppressive agents, and being useful in the treatment in transplant rejection, certain inflammatory diseases, cardiovascular disorders, allergic conditions, disorders of the central nervous system and cell proliferative disorders.

2 Claims, 5 Drawing Sheets

OTHER PUBLICATIONS

Baba et al., "Synergistic Antiviral Effects of Antiherpes Compounds and Human Leukocyte Interferon on Varicella-Zoster Virus in Vitro," *Antimicrob. Agents Chemother.* 25:515-517 (1984).

Abstract XP-002313350, Kaldrikyan, M.A. et al., "Pteridine Derivatives", 1 page, (1976).

Matter et al., "Structural Requirements for Inhibition of the Neuronal Nitric Oxide Synthase (NOS-I): 3D-QSAR Analysis of 4-Oxo- and 4-Amino-Pteridine-Based Inhibitors", *J. Med. Chem.* 45:2923-2941 (2002).

Nicolaus, B.J.R., "Symbiotic Approach to Drug Design", *Decision Making in Drug Research*, 173-186 (1983).

Yao and Pfleiderer, "Pteridines. Protection of Pteridines", *Helvetica Chimica Acta*, 86:1-12 (2003).

Y. Landry, "Pharmacologie. Descibles vers l'indication therapeutique" *Cours et exercise*, p. 177, paragraphs 2, 3 (2003); XP-002313503.

Beilstein search results, XP-002296934, 11 pages.

Beilstein search results, XP-002296933, 3 pages.

Beers and Berkow, "The Merck Manual of Diagnosis and Therapy 17th Edition," 1474-1476 (1999); XP-002313611.

Beers and Berkow, "The Merck Manual of Diagnosis and Therapy 17th Edition," 953-954 (1999); XP-002313612.

Boon, "Pteridines. Part IV.* Derivatives of 2:4-Diaminopteridine and Related Compounds," *J. Chem. Soc.* 2146-2158 (1957).

Chou and Talalay, "Quantitative Analysis of Dose-Effect Relationships: The Combined Effects of Multiple Drugs or Enzyme Inhibitors," *Adv. Enzyme Regul.* 22:27-55 (1984).

Elion et al., "Antagonists of Nucleic Acid Derivatives. VIII. Synergism in Combinations of Biochemically Related Antimetabolites," *J. Biol. Chem.* 208:477-488 (1954).

Landauer and Rydon, "A Convenient Synthesis of Some 4-Substituted 5-Aminopyrimidines," *J. Chem. Soc.* 3721-3722 (1953).

Lin et al., "Use of the Methylxanthine Derivative A802715 in Transplantation Immunology, I. Strong in Vitro Inhibitory Effects on CD28-Costimulated T Cell Activities," *Transplantation* 63:1813-1819 (1997).

Lin et al., "Use of the Methylxanthine Derivative A802715 in Transplantation Immunology, II. In Vivo Experiments," *Transplantation* 63:1734-1738 (1997).

Mohr et al., "Pteridines: Synthesis and Properties of 6-Thioxanthopterin and 7-Thioisoxanthopterin," *Helv. Chim. Acta* 75:2317-2326 (1992).

Moreb and Zucali, "The Therapeutic Potential of Interleukin-1 and Tumor Necrosis Factor on Hematopoietic Stem Cells," *Leuk. Lymph.* 8:267-275 (1992).

Murata et al.,"A Facile Method for Regioselective 6,7-Disubstitution of Pteridine," *Heterocycles* 53: 1259-1262 (2000).

Pfleiderer and Lohrmann, "Pteridine, XII: Synthese von 2-Amino-4-Alkoxy-Pteridinen," *Chem. Ber.* 94:12-18 (1961).

Sato and Fukuya, "Studies on Pyrazines. Part 37. $^1$Synthesis of 6-Propionylpteridine-2,4 (1H,3H)-dione and its 1- and/or 3-Methyl Derivatives from Marine Natural Products," *J. Chem. Soc., Perkin Trans.* 1:89-95 (2000).

PCT International Preliminary Examination Report, Filed Dec. 28, 1999 as PCT/EP99/10320, 7 pages.

\* cited by examiner

IMMUNOSUPPRESSIVE EFFECTS OF PTERIDINE DERIVATIVES

CROSS REFERENCE TO RELATED APPLICATIONS

This application is a continuation-in-part of pending U.S. application Ser. No. 09/869,468, filed Oct. 10, 2001 now abandoned, which is the National Stage of International Application No. PCT/EP99/10320, filed Dec. 28, 1999, which was published in English under PCT Article 21(2), and which claims the benefit of U.S. provisional application No. 60/113,989 filed Dec. 28, 1998; the disclosures of which are incorporated by reference in their entirety.

The invention relates to a class of novel pteridines. The invention further relates to pharmaceutical compositions including a broad class of pteridines especially for the prevention and/or the treatment of pathologic conditions such as, but not limited to, immune and auto-immune disorders, organ and cells transplant rejections, cell proliferative disorders, cardiovascular disorders, disorders of the central nervous system and viral diseases.

The invention further relates to combined pharmaceutical preparations comprising one or more pteridines and one or more known immunosuppressant drugs or antineoplastic drugs or anti-viral drugs.

This invention also relates to a method for the prevention and/or treatment of pathologic conditions such as, but not limited to, immune and autoimmune disorders, organ and cells transplant rejections, cell proliferative disorders, cardiovascular disorders, disorders of the central nervous system and viral diseases by the administration of an effective amount of a specific pteridine optionally combined with one or more known immunosuppressant drugs or antineoplastic drugs or anti-viral drugs.

BACKGROUND OF THE INVENTION

Several 2,4-diaminopteridine derivatives being substituted in the 6-position and/or the 7-position of the pteridine ring (according to standard atom numbering for said ring) are known in the art, e.g. from various sources of literature including Swiss Patent No. 231,852; British Patent No. 763,044; U.S. Pat. No. 2,512,572; U.S. Pat. No. 2,581,889; U.S. Pat. No. 2,665,275; U.S. Pat. No. 2,667,486; U.S. Pat. No. 2,940,972; U.S. Pat. No. 3,081,230 and U.S. Pat. No. 5,047,405. Some of these substituted 2,4-diaminopteridine derivatives were disclosed in relationship with various medical uses, such as bacterial growth inhibitors, antineoplastic agents, anti-schistosomiasis activity, coronary dilating activity, diuretic and hypotensive activity, and anti-amnesic activity. In particular, U.S. Pat. No. 2,940,972 and EP-A-362,645 disclose very specific 2,4-diaminopteridine derivatives being substituted by piperidinyl, morpholinyl or pyrrolidinyl in the 7-position of the pteridine ring.

Specific 2-aminopteridine derivatives wherein the 4-position of the pteridine ring is substituted with an alkoxy group and the 6-position is also substituted are also known in the art, although without any medical utility. For instance, U.S. Pat. No. 2,740,784 discloses such derivatives wherein the 6-substituent is an acetal; J. Chem. Soc. (1957) 2146–2158 discloses 2-dimethylamino-4-ethoxy-6-phenylpteridine as a compound with a melting point of 200° C.; Arm. Khim. J. discloses 2-amino-4-ethoxy-6,7-diphenylpteridine; Helv. Chem. Acta (1992) 75:2317–2326 discloses 2-amino-4-pentoxy-6-methylthiopteridine. Furthermore, International Patent Application published as WO 01/19825 discloses 2-phenylamino and 2-phenylsulfoxide pteridines wherein the 7-position is substituted with an amide as being useful inhibitors of cell cycle regulatory kinases.

Nevertheless, there still is a need in the art for specific and highly therapeutically active compounds, such as, but not limited to, drugs for treating immune and autoimmune disorders, organ and cells transplant rejections, cell proliferative disorders, cardiovascular disorders, disorders of the central nervous system and viral diseases. In particular, there is a need in the art to provide immunosuppressive compounds or antineoplastic drugs or anti-viral drugs which are active in a minor dose in order to replace existing drugs having significant side effects and to decrease treatment costs.

Currently used immunosuppressive drugs include antiproliferative agents, such as methotrexate (a 2,4-diaminopteridine derivative disclosed by U.S. Pat. No. 2,512,572), azathioprine, and cyclophosphamide. Since these drugs affect mitosis and cell division, they have severe toxic effects on normal cells with high turn-over rate such as bone marrow cells and the gastrointestinal tract lining. Accordingly, marrow depression and liver damage are common side effects of these antiproliferative drugs.

Anti-inflammatory compounds used to induce immunosuppression include adrenocortical steroids such as dexamethasone and prednisolone. The common side effects observed with the use of these compounds are frequent infections, abnormal metabolism, hypertension, and diabetes.

Other immunosuppressive compounds currently used to inhibit lymphocyte activation and subsequent proliferation include cyclosporine, tacrolimus and rapamycin. Cyclosporine and its relatives are among the most commonly used immunosuppressant drugs. Cyclosporine is typically used for preventing or treating organ rejection in kidney, liver, heart, pancreas, bone marrow, and heart-lung transplants, as well as for the treatment of autoimmune and inflammatory diseases such as Crohn's disease, aplastic anemia, multiple-sclerosis, myasthenia gravis, uveitis, biliary cirrhosis, etc. However, cyclosporines suffer from a small therapeutic dose window and severe toxic effects including nephrotoxicity, hepatotoxicity, hypertension, hirsutism, cancer, and neurotoxicity.

Additionally, monoclonal antibodies with immunosuppressant properties, such as OKT3, have been used to prevent and/or treat graft rejection. Introduction of such monoclonal antibodies into a patient, as with many biological materials, induces several side-effects, such as dyspnea. Within the context of many life-threatening diseases, organ transplantation is considered a standard treatment and, in many cases, the only alternative to death. The immune response to foreign cell surface antigens on the graft, encoded by the major histo-compatibility complex (hereinafter referred as MHC) and present on all cells, generally precludes successful transplantation of tissues and organs unless the transplant tissues come from a compatible donor and the normal immune response is suppressed. Other than identical twins, the best compatibility and thus, long term rates of engraftment, are achieved using MHC identical sibling donors or MHC identical unrelated cadaver donors. However, such ideal matches are difficult to achieve. Further, with the increasing need of donor organs an increasing shortage of transplanted organs currently exists. Accordingly, xenotransplantation has emerged as an area of intensive study, but faces many hurdles with regard to rejection within the recipient organism.

The host response to an organ allograft involves a complex series of cellular interactions among T and B lymphocytes as well as macrophages or dendritic cells that recognize and are activated by foreign antigen. Co-stimulatory factors, primarily cytokines, and specific cell-cell interactions, provided by activated accessory cells such as macrophages or dendritic cells are essential for T-cell proliferation. These macrophages and dendritic cells either directly adhere to T-cells through specific adhesion proteins or secrete cytokines that stimulate T-cells, such as IL-12 and IL-15. Accessory cell-derived co-stimulatory signals stimulate activation of interleukin-2 (IL-2) gene transcription and expression of high affinity IL-2 receptors in T-cells. IL-2 is secreted by T lymphocytes upon antigen stimulation and is required for normal immune responsiveness. IL-2 stimulates lymphoid cells to proliferate and differentiate by binding to IL-2 specific cell surface receptors (IL-2R). IL-2 also initiates helper T-cell activation of cytotoxic T-cells and stimulates secretion of interferon-γ which in turn activates cytodestructive properties of macrophages. Furthermore, IFN-γ and IL-4 are also important activators of MHC class II expression in the transplanted organ, thereby further expanding the rejection cascade by enhancing the immunogenicity of the grafted organ The current model of a T-cell mediated response suggests that T-cells are primed in the T-cell zone of secondary lymphoid organs, primarily by dendritic cells. The initial interaction requires cell to cell contact between antigen-loaded MHC molecules on antigen-presenting cells (hereinafter referred as APC) and the T-cell receptor/CD3 complex on T-cells. Engagement of the TCR/CD3 complex induces CD154 expression predominantly on CD4 T-cells that in turn activate the APC through CD40 engagement, leading to improved antigen presentation. This is caused partly by upregulation of CD80 and CD86 expression on the APC, both of which are ligands for the important CD28 co-stimulatory molecule on T-cells. However, engagement of CD40 also leads to prolonged surface expression of MHC-antigen complexes, expression of ligands for 4-1 BB and OX-40 (potent co-stimulatory molecules expressed on activated T-cells). Furthermore, CD40 engagement leads to secretion of various cytokines (e.g., IL-12, IL-15, TNF-α, IL-1, IL-6, and IL-8) and chemokines, all of which have important effects on both APC and T-cell activation and maturation. Similar mechanisms are involved in the development of auto-immune disease, such as type I diabetes. In humans and non-obese diabetic mice, insulin-dependent diabetes mellitus results from a spontaneous T-cell dependent auto-immune destruction of insulin-producing pancreatic .beta. cells that intensifies with age. The process is preceded by infiltration of the islets with mono-nuclear cells (insulitis), primarily composed of T lymphocytes. A delicate balance between auto-aggressive T-cells and suppressor-type immune phenomena determines whether expression of auto-immunity is limited to insulitis or not. Therapeutic strategies that target T-cells have been successful in preventing further progress of the auto-immune disease. These include neonatal thymectomy, administration of cyclosporine, and infusion of anti-pan T-cell, anti-CD4, or anti-CD25 (IL-2R) monoclonal antibodies. The aim of all rejection prevention and auto-immunity reversal strategies is to suppress the patient's immune reactivity to the antigenic tissue or agent, with a minimum of morbidity and mortality. Accordingly, a number of drugs are currently being used or investigated for their immunosuppressive properties. As discussed above, the most commonly used immunosuppressant is cyclosporine, which however has numerous side effects. Accordingly, in view of the relatively few choices for agents effective at immunosuppression with low toxicity profiles and manageable side effects, there exists a need in the art for identification of alternative immunosuppressive agents and for agents acting as complement to calcineurin inhibition.

The metastasis of cancer cells represents the primary source of clinical morbidity and mortality in the large majority of solid tumors. Metastasis of cancer cells may result from the entry of tumor cells into either lymphatic or blood vessels. Invasion of lymphatic vessels results in metastasis to regional draining lymph nodes. From the lymph nodes, melanoma cells for example tend to metastasize to the lung, liver, and brain. For several solid tumors, including melanoma, the absence or the presence of lymph nodes metastasis is the best predictor of patient survival. Presently, to our knowledge, no treatment is capable of preventing or significantly reducing metastasis. Hence, there is a need in the art for compounds having such anti-metastasis effect for a suitable treatment of cancer patients.

In the field of allergy, IgE is well known for inducing allergy mainly by stimulating mast cells to release histamine. Also, asthma, being characterized by inflammation of airway and bronchospasm, is mainly induced by Th2 cytokines such as IL-5, IL-10 or IL-13. Therefore there is a need in the art for compounds that efficiently inhibit the release of these Th2 cytokines.

There is also a need in the art to improve therapeutic efficiency by providing pharmaceutical compositions or combined preparations exhibiting a synergistic effect as a result of combining two or more immunosuppressant drugs, or antineoplastic drugs or anti-viral drugs or anti-histamine drugs.

Meeting these various needs in the art constitutes the main goal of the present invention.

SUMMARY OF THE INVENTION

In a first embodiment, the present invention relates to a group of novel pteridine derivatives having the general formula (I):

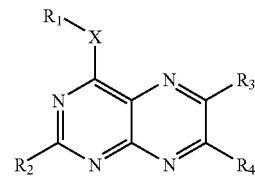

wherein X represents an oxygen atom or a group with the formula $S(O)_m$ wherein m is an integer from 0 to 2, or a group with the formula NZ and wherein:

$R_1$ is a group selected from the group consisting of $C_{1-7}$ alkyl, $C_{2-7}$ alkenyl, $C_{2-7}$ alkynyl, $C_{3-10}$ cycloalkyl, $C_{3-10}$ cycloalkenyl, aryl, alkylaryl, arylalkyl, heterocyclic, heterocyclic-substituted alkyl and alkyl-substituted heterocyclic, each of said groups being optionally substituted with one or more substituents selected from the group consisting of halogen, $C_{1-4}$ alkyl, $C_{1-4}$ alkoxy, $C_{2-7}$ alkenyl, $C_{2-7}$ alkynyl, halo $C_{1-4}$ alkyl, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxyl, sulfhydryl, nitro, hydroxylamino, mercaptoamino, cyano, carboxylic acid or esters or thioesters or amides or thioamides or halides or anhydrides thereof, thiocarboxylic acid or esters or thioesters or amides or thioamides or halides or anhydrides thereof, carbamoyl, thiocarbamoyl, ureido, thio-ureido, amino, cycloalkylamino, alkenylamino, cycloalkenylamino, alkynylamino, arylamino, arylalkylamino, hydroxyalkylamino, mercaptoalkyl-amino, heterocyclic amino, hydrazino, alkylhydrazino and phenyl-hydrazino; or $R_1$ is a carboxyalkyl, carboxyaryl, thiocarboxyaryl or thiocarboxyalkyl group;

Z is a group independently defined as $R_1$ or Z is hydrogen or the group NZ together with $R_1$ is either hydroxylamino or an optionally substituted heterocyclic group containing at least one nitrogen atom;

$R_2$ is selected from the group consisting of amino; acylamino; thioacylamino; carbamoyl; thiocarbamoyl, ureido; thio-ureido, sulfonamido; hydroxylamino; alkoxyamino; thioalkylamino; mercaptoamino, hydrazino; alkylhydrazino; phenylhydrazino; optionally substituted heterocyclic radicals; $C_{3-7}$ alkylamino; arylamino; arylalkylamino; cycloalkylamino; alkenylamino; cycloalkenylamino; heterocyclic amino; hydroxyalkylamino; mercaptoalkylamino; $C_{1-7}$ alkoxy; $C_{3-10}$ cycloalkoxy; thio $C_{1-7}$ alkyl; arylsulfoxide; arylsulfone; heterocyclic sulfoxide; heterocyclic sulfone; thio $C_{3-10}$ cycloalkyl; aryloxy; arylthio; arylalkyloxy; arylalkylthio; oxyheterocyclic and thioheterocyclic radicals;

$R_4$ is an atom or a group selected from the group consisting of hydrogen; halogen; $C_{1-7}$ alkyl; $C_{2-7}$ alkenyl; $C_{2-7}$ alkynyl; halo $C_{1-7}$ alkyl; carboxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; mercapto-amino; acylamino; thio-acylamino; alkoxyamino; thioalkylamino; acetal; thioacetal; carboxylic acid; carboxylic acid esters, thioesters, halides, anhydrides, amides and thioamides; thiocarboxylic acid; thiocarboxylic acid esters, thioesters, halides, anhydrides, amides and thioamides; hydroxyl; sulfhydryl; nitro; cyano; carbamoyl; thiocarbamoyl, ureido; thio-ureido; alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters, thioesters, halides, anhydrides, amides and thioamides thereof; phenyl substituted with one or more substituents selected from the group consisting of $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thio-ureido, sulfonamido, hydroxylamino, alkoxyamino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; aryl groups other than phenyl, the said aryl groups being optionally substituted with one or more substituents selected from the group consisting of halogen, $C_{1-7}$ alkyl, $C_{1-7}$ alkoxy, $C_{2-7}$ alkenyl, $C_{2-7}$ alkynyl, halo $C_{1-7}$ alkyl, nitro, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thio-ureido, sulfonamido, hydroxylamino, alkoxyamino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; optionally substituted heterocyclic radicals other than piperidinyl, morpholinyl or pyrrolidinyl, i.e. preferably selected from the group consisting of oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thio-urazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl, phtalidyl, phtalimidinyl, phtalazonyl, alloxazinyl, xanthionyl, isatyl, isopyrazolyl, isopyrazolonyl, urazolyl, urazinyl, uretinyl, uretidinyl, succinyl, succinimido, benzylsultimyl and benzylsultamyl; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), thiocarbonyl, alcohol (hydroxyl), thiol, ether, thio-ether, acetal, thio-acetal, amino, imino, oximino, alkyloximino, amino-acid, cyano, acylamino, thioacylamino, carbamoyl, thiocarbamoyl, ureido, thio-ureido, carboxylic acid or ester or thioester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfinyl, sulfonamido and halogen; branched or straight, saturated or unsaturated aliphatic chains of 1 to 7 carbon atoms optionally containing one or more functions selected from the group consisting of carbonyl (oxo), thiocarbonyl, alcohol (hydroxyl), thiol, ether, thio-ether, acetal, thio-acetal, amino, imino, oximino, alkyloximino, aminoacid, cyano, acylamino; thioacylamino; carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxy-alkylamino, mercaptoalkylamino, heterocyclic amino, hydrazino, alkylhydrazino, phenylhydrazino, sulfonyl, sulfinyl, sulfonamido and halogen; and $R_3$ is an atom or a group selected from the group consisting of fluoro, bromo, iodo, $C_{2-7}$ alkyl; $C_{2-7}$ alkenyl; $C_{2-7}$ alkynyl; halo $C_{1-7}$ alkyl; $C_{1-7}$ alkoxy; $C_{3-10}$ cycloalkoxy; aryloxy; arylalkyloxy; oxyheterocyclic; heterocyclic-substituted alkyloxy; thio $C_{2-7}$ alkyl; thio $C_{3-10}$ cycloalkyl; thioaryl; thioheterocyclic; arylalkylthio; heterocyclic-substituted alkylthio; hydroxy-lamino; alkoxyamino; thioalkylamino; mercaptoamino; acylamino; thio-acylamino; thio-acetal; carboxylic acid; carboxylic acid esters, thioesters, amides, halides, anhydrides and thioamides; thiocarboxylic acid; thiocarboxylic acid esters, thioesters, amides, halides, anhydrides and thioamides; hydroxyl; sulfhydryl; nitro; carbamoyl; thiocarbamoyl; ureido; thio-ureido; amino; alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters, thioesters, amides and thioamides thereof; aryl optionally substituted with one or more substituents selected from the group consisting of halogen, $C_{1-7}$ alkyl, $C_{1-7}$ alkoxy, $C_{2-7}$ alkenyl, $C_{2-7}$ alkynyl, halo $C_{1-7}$ alkyl, nitro, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thio-ureido, sulfonamido, hydroxylamino, mercaptoamino, alkoxyamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino and phenylhydrazino; optionally substituted heterocyclic radicals; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), thiocarbonyl, alcohol (hydroxyl), thiol, ether, thio-ether, acetal, thioacetal, amino, imino, oximino, alkyloximino, amino-acid, cyano, carboxylic acid or ester or thioester or amide, nitro, thio $C_{1-7}$ alkyl, thio $C_{3-10}$ cycloalkyl, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen; branched or straight, saturated or unsaturated aliphatic chains of 2 to 7 carbon atoms optionally containing one or more functions selected from the group consisting of thiocarbonyl, alcohol (hydroxyl), thiol, ether, thio-ether, thio-acetal, amino, imino, oximino, alkyloximino, amino-acid, cyano, acylamino, thioacylamino, carbamoyl, thiocarbamoyl, ureido, thio-ureido, carboxylic acid or ester or thioester or halide or anhydride or amide, thio carboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfinyl, sulfonamido and halogen; or $R_3$ together with $R_4$ forms a homocyclic or heterocyclic radical such as, but not limited to, indolyl, dihydroxypyrimidyl or tetramethylene;

and/or a pharmaceutically acceptable addition salt thereof and/or a stereoisomer thereof and/or a mono- or a di-N-oxide thereof and/or a solvate thereof and/or a dihydro- or tetrahydropteridine derivative thereof.

The above novel compounds have in common the structural features present in the general formula (I), in particular they are at least trisubstituted in positions 2, 4 and 6 of the pteridine ring. They also have a potential specific biological activity profile and consequent usefulness in medicinal chemistry.

In a second embodiment, the present invention relates to the unexpected finding that at least one desirable biological property such as, but not limited to, the ability to decrease the proliferation of lymphocytes, or to decrease T-cell activation, or to decrease B-cell or monocytes or macrophages activation, or to inhibit the release of certain cytokines, is a common feature which is not only present in the group of novel compounds defined in the general formula (I), but also in a group of pteridine derivatives which is broader than the said group of novel compounds. As a consequence, the invention relates to pharmaceutical compositions comprising as an active principle at least one pteridine derivative having the general formula (II):

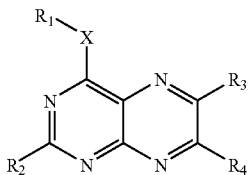

wherein X represents an oxygen atom or a group with the formula $S(O)_m$ wherein m is an integer from 0 to 2, or a group with the formula NZ and wherein:

$R_1$ is a group selected from the group consisting of $C_{1-7}$ alkyl, $C_{2-7}$ alkenyl, $C_{2-7}$ alkynyl, $C_{3-10}$ cycloalkyl, $C_{3-10}$ cycloalkenyl, aryl, alkylaryl, arylalkyl, heterocyclic, heterocyclic-substituted alkyl and alkyl-substituted heterocyclic, each of said groups being optionally substituted with one or more substituents selected from the group consisting of halogen, $C_{1-4}$ alkyl, $C_{1-4}$ alkoxy, $C_{2-7}$ alkenyl, $C_{2-7}$ alkynyl, halo $C_{1-4}$ alkyl, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxyl, sulfhydryl, nitro, hydroxylamino, mercaptoamino, cyano, carboxylic acid or esters or thioesters or amides or thioamides or halides or anhydrides thereof, thiocarboxylic acid or esters or thioesters or amides or thioamides or halides or anhydrides thereof, carbamoyl, thiocarbamoyl, ureido, thio-ureido, amino, cycloalkylamino, alkenylamino, cycloalkenylamino, alkynylamino, arylamino, arylalkylamino, hydroxylalkylamino, mercaptoalkyl-amino, heterocyclic amino, hydrazino, alkylhydrazino and phenyl-hydrazino; or $R_1$ is a carboxyalkyl, carboxyaryl, thiocarboxyaryl or thiocarboxyalkyl group;

Z is a group independently defined as $R_1$ or Z is hydrogen or the group NZ together with $R_1$ is either hydroxylamino or an optionally substituted heterocyclic group containing at least one nitrogen atom;

$R_2$ is selected from the group consisting of amino; acylamino; thioacylamino; carbamoyl; thiocarbamoyl, ureido; thioureido, sulfonamido; hydroxylamino; alkoxyamino; thioalkylamino; mercaptoamino, hydrazino; alkylhydrazino; phenylhydrazino; optionally substituted heterocyclic radicals; $C_{3-7}$ alkylamino; arylamino; arylalkylamino; cycloalkylamino; alkenylamino; cycloalkenylamino; heterocyclic amino; hydroxyalkylamino; mercaptoalkylamino; $C_{1-7}$ alkoxy; $C_{3-10}$ cycloalkoxy; thio $C_{1-7}$ alkyl; arylsulfoxide; arylsulfone; heterocyclic sulfoxide; heterocyclic sulfone; thio $C_{3-10}$ cycloalkyl; aryloxy; arylthio; arylalkyloxy; arylalkylthio; oxyheterocyclic and thioheterocyclic radicals, $R_4$ is an atom or a group selected from the group consisting of hydrogen; halogen; $C_{1-7}$ alkyl; $C_{2-7}$ alkenyl; $C_{2-7}$ alkynyl; halo $C_{1-7}$ alkyl; carboxy $C_{1-7}$ alkyl; acetoxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; mercapto-amino; acylamino; thio-acylamino; alkoxyamino; thioalkylamino; acetal; thio-acetal; carboxylic acid; carboxylic acid esters, thioesters, halides, anhydrides, amides and thioamides; thiocarboxylic acid; thiocarboxylic acid esters, thioesters, halides, anhydrides, amides and thioamides; hydroxyl; sulfhydryl; nitro; cyano; carbamoyl; thiocarbamoyl, ureido; thio-ureido; alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters, thioesters, halides, anhydrides, amides and thioamides thereof; phenyl substituted with one or more substituents selected from the group consisting of $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thio-ureido, sulfonamido, hydroxylamino, alkoxyamino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; aryl groups other than phenyl, the said aryl groups being optionally substituted with one or more substituents selected from the group consisting of halogen, $C_{1-7}$ alkyl, $C_{1-7}$ alkoxy, $C_{2-7}$ alkenyl, $C_{2-7}$ alkynyl, halo $C_{1-7}$ alkyl, nitro, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thioureido, sulfonamido, hydroxylamino, alkoxyamino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; optionally substituted heterocyclic radicals other than piperidinyl, morpholinyl or pyrrolidinyl, i.e. preferably selected from the group consisting of oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benziso-alloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl, phtalidyl, phtalimidinyl, phtalazonyl, alloxazinyl, xanthionyl, isatyl, isopyrazolyl, isopyrazolonyl, urazolyl, urazinyl, uretinyl, uretidinyl, succinyl, succinimido, benzylsultimyl and benzylsultamyl; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), thiocarbonyl, alcohol (hydroxyl), thiol, ether, thio-ether, acetal, thioacetal, amino, imino, oximino, alkyloximino, aminoacid, cyano, acylamino, thioacylamino, carbamoyl, thiocarbamoyl, ureido, thio-ureido, carboxylic acid or ester or thioester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfinyl, sulfonamido and halogen; branched or straight, saturated or unsaturated aliphatic chains of 2 to 7 carbon atoms optionally containing one or more functions selected from the group consisting of carbonyl (oxo), thiocarbonyl, alcohol (hydroxyl), thiol, ether, thio-ether, acetal, thio-acetal, amino, imino, oximino, alkyl-oximino, amino-acid, cyano, acylamino; thioacylamino; carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxy-alkylamino, mercaptoalkylamino, heterocyclic amino, hydrazino, alkylhydrazino, phenylhydrazino, sulfonyl, sulfinyl, sulfonamido and halogen; and $R_3$ is an atom or a group defined as $R_4$ or $R_3$ is selected from the group consisting of morpholinyl, amino, hydrogen, methyl, thiomethyl and chloro; or $R_3$ together with $R_4$ forms a homocyclic or heterocyclic radical such as, but not limited to, indolyl, dihydroxypyrimidyl or tetramethylene;

and/or a pharmaceutically acceptable addition salt thereof and/or a stereoisomer thereof and/or a mono- or a di-N-oxide thereof and/or a solvate and/or a dihydro- or tetrahydropteridine derivative thereof.

Compounds of formula (II) are highly active immunosuppressive agents, antineoplastic agents, anti-allergic agents or anti-viral agents which, together with one or more pharmaceutically acceptable carriers, may be formulated into pharmaceutical compositions for the prevention or treatment of pathologic conditions such as, but not limited to, immune and autoimmune disorders, organ and cells transplant rejections, allergic conditions, cell proliferative disorders, cardiovascular disorders, disorders of the central nervous system and viral diseases.

In a further embodiment, the present invention relates to combined preparations containing at least one compound of formula (II) and one or more drugs such as immunosuppressant and/or immunomodulator drugs, antineoplastic drugs, anti-histamines, inhibitors of agents causative of allergic conditions, or antiviral agents. In a further embodiment, the present invention relates to the prevention or treatment of the above-cited pathologic conditions by administering to the patient in need thereof an effective amount of a compound of general formula (II), optionally in the form of a pharmaceutical composition or combined preparation with another suitable drug.

In a still further embodiment, the present invention relates to various processes and methods for making the novel pteridine derivatives defined in general formula (1), as well as their pharmaceutically acceptable salts, N-oxides, solvates, enantiomers and dihydro- and tetrahydroderivatives.

DEFINITIONS

Figure 1:
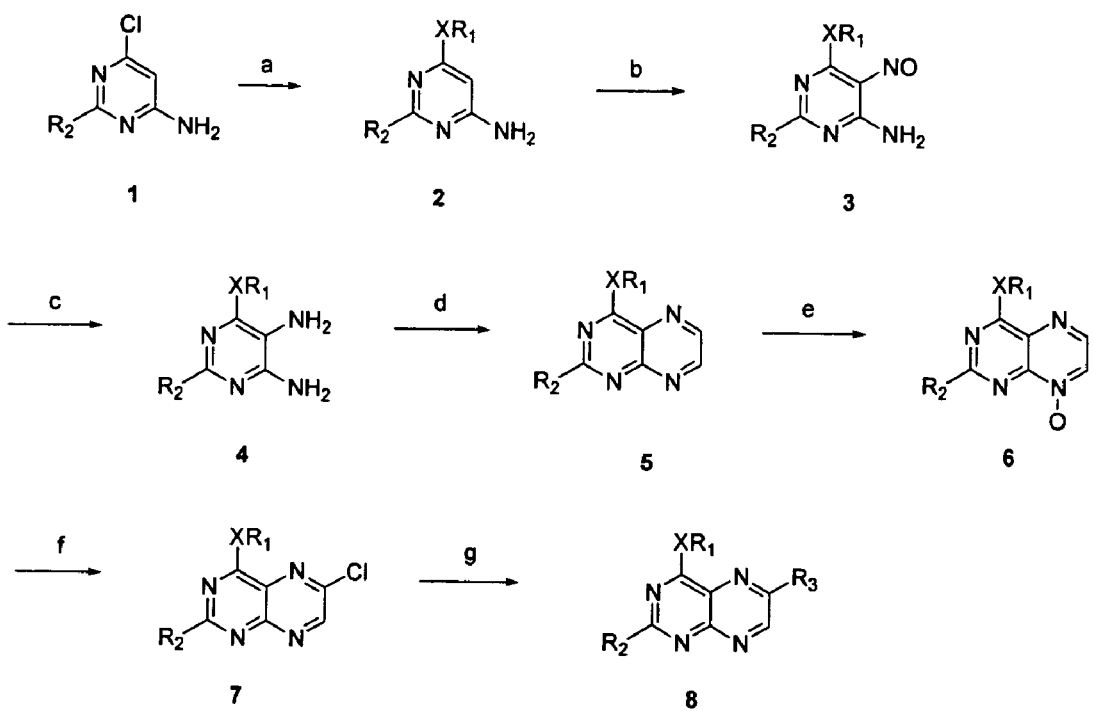
FIGS. 1 and 2 represent alternative schemes for preparing 2,4,6-trisubstituted pteridine derivatives according to this invention.

Unless otherwise stated herein, the term "trisubstituted" means that three of the carbon atoms being in positions 2, 4 and 6 or, alternatively, in positions 2, 4 and 7 of the pteridine ring (according to standard atom numbering for the pteridine ring) are substituted with an atom or group other than hydrogen. The term "tetrasubstituted" means that all four carbon atoms being in positions 2, 4, 6 and 7 of the pteridine ring are substituted with an atom or group other than hydrogen.

As used herein with respect to a substituting radical, and unless otherwise stated, the terms "$C_{1-7}$ alkyl" or "aliphatic saturated hydrocarbon radicals with 1 to 7 carbon atoms" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (ter-butyl), 2-methylbutyl, n-pentyl, dimethylpropyl, n-hexyl, 2-methylpentyl, 3-methylpentyl, n-heptyl and the like; the term "$C_{1-4}$ alkyl" designate the corresponding radicals with only 1 to 4 carbon atoms, and so on.

As used herein with respect to a substituting radical, and unless otherwise stated, the term $C_{1-7}$ alkylene means the divalent hydrocarbon radical corresponding to the above defined $C_{1-7}$ alkyl, such as methylene, bis(methylene), tris (methylene), tetramethylene, hexamethylene and the like.

As used herein with respect to a substituting radical, and unless otherwise stated, the terms "$C_{3-10}$ cycloalkyl" and "cycloaliphatic saturated hydrocarbon radical with 3 to 10 carbon atoms" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the terms "aryl" and "aromatic substituent" are interchangeable and designate any mono- or polyaromatic monovalent hydrocarbon radical having from 6 up to 30 carbon atoms such as but not limited to phenyl, naphthyl, anthracenyl, adamantyl, phenantracyl, fluoranthenyl, chrysenyl, pyrenyl, biphenylyl, terphenyl, picenyl and the like, including spiro hydrocarbon radicals and fused benzo —$C_{5-8}$ cycloalkyl radicals (the latter being as defined above) such as, for instance, indanyl, 1,2,3,4-tetrahydronaphtalenyl, fluorenyl and the like.

As used herein with respect to a substituting radical such as the combination of $R_3$ and $R_4$, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring.

As used herein with respect to a substituting radical, and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in a 3 to 10 membered ring (and optionally one or more heteroatoms attached to one or more carbon atoms of said ring, for instance in the form of a carbonyl or thiocarbonyl group) and/or to one or more heteroatoms of said ring, for instance in the form of a sulfone, sulfoxide, N-oxide, phosphate, phosphonate or selenium oxide, each said heteroatom being independently selected from the group consisting of nitrogen, oxygen, sulfur, selenium and phosphorus, including benzo-fused heterocyclic radicals, such as but not limited to oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thio-urazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benziso-alloxazinyl, benzocoumarinyl, thiocoumarinyl, phenometoxazinyl, phenoparoxazinyl, phentriazinyl, thiodiazinyl, thiodiazolyl, indoxyl, thio-indoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of the said ring may be substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercapto-alkylamino, heterocyclic amino, hydrazino, alkylhydrazino, phenyl-hydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 membered ring, heterocyclic radicals may be sub-divided into heteroaromatic (or "heteroaryl") radicals and non-aromatic heterocyclic radicals; when a heteroatom of the said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a $C_{1-7}$ alkyl radical, respectively a $C_{3-10}$ cycloalkyl, aryl, arylalkyl or heterocyclic radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl, cresoxy and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like; the term "halo $C_{1-4}$ alkyl" designate the corresponding radical with only 1 to 4 carbon atoms, and so on.

As used herein with respect to a substituting radical, and unless otherwise stated, the terms "$C_{2-7}$ alkenyl" and "aliphatic unsaturated hydrocarbon radical with 2 to 7 carbon atoms" are interchangeable and designate a straight and branched acyclic hydrocarbon monovalent radical having one or more ethylenical unsaturations and having from 2 to 7 carbon atoms such as, for example, vinyl, 2-propenyl, 3-butenyl, 2-butenyl, 2-pentenyl, 3-pentenyl, 3-methyl-2-butenyl, 3-hexenyl, 2-hexenyl, 2-heptenyl, butadienyl, pentadienyl, hexadienyl, heptadienyl, heptatrienyl and the like, including all possible isomers thereof; the term "$C_{3-7}$ alkenyl" designate the corresponding radical with only 3 to 7 carbon atoms, and so on.

As used herein with respect to a substituting radical, and unless otherwise stated, the terms "$C_{3-10}$ cycloalkenyl" and "cycloaliphatic unsaturated hydrocarbon radical with 3 to 10 carbon atoms" are interchangeable and mean a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl and the like, or a $C_{7-10}$ polycyclic mono or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and having from 2 to 20 carbon atoms such as, for example, acetylenyl, 2-propynyl, 3-butynyl, 2-butynyl, 2-pentynyl, 3-pentynyl, 3-methyl-2-butynyl, 3-hexynyl, 2-hexynyl and the like and all possible isomers thereof.

As used herein with respect to a substituting radical, and unless otherwise stated, the terms "arylalkyl" and "heterocyclic-substituted alkyl" refer to an aliphatic saturated hydrocarbon monovalent radical, preferably a $C_{1-7}$ alkyl or a $C_{3-10}$ cycloalkyl such as defined above, onto which an aryl radical or respectively a heterocyclic radical (such as defined above) is already bonded, such as but not limited to benzyl, pyridylmethyl, pyridylethyl, 2-(2-pyridyl)isopropyl, oxazolylbutyl, 2-thienylmethyl and 2-furylmethyl.

As used herein with respect to a substituting radical, and unless otherwise stated, the term "alkylaryl" and "alkyl-substituted heterocyclic" refer to an aryl radical or respectively a heterocyclic radical (such as defined above) onto which is (are) already bonded one or more aliphatic saturated hydrocarbon monovalent radicals, preferably $C_{1-7}$ alkyl radicals or $C_{3-10}$ cycloalkyl radicals as defined above such as, but not limited to, o-toluyl, mtoluyl, p-toluyl, mesityl and 2,4,6-trimethylphenyl.

As used herein with respect to a substituting radical, and unless otherwise stated, the terms "alkylamino", "cycloalkylamino", "alkenylamino", "cycloalkenylamino", "arylamino", "arylalkylamino", "heterocyclic amino", "hydroxyalkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic, mono- or polyhydroxy $C_{1-7}$ alkyl, mono- or polymercapto $C_{1-7}$ alkyl or $C_{2-7}$ alkynyl radical(s) (each of them as defined herein, respectively) is/are attached to a nitrogen atom through a single bond or, in the case of heterocyclic, include a nitrogen atom, such as but not limited to, anilino, benzylamino, methylamino, dimethylamino, ethylamino, diethylamino, isopropylamino, propenylamino, n-butylamino, ter-butylamino, dibutylamino, morpholinoalkylamino, morpholinyl, piperidinyl, piperazinyl, hydroxymethylamino, β-hydroxyethylamino and ethynylamino; this definition also includes mixed disubstituted amino radicals wherein the nitrogen atom is attached to two such radicals belonging to two different sub-set of radicals, e.g. an alkyl radical and an alkenyl radical, or to two different radicals within the same sub-set of radicals, e.g. methylethylamino; the term "$C_{3-7}$ alkylamino" designates the corresponding radical with only 3 to 7 carbon atoms in the alkyl group(s) attached to nitrogen, for instance di-isopropylamino, and so on; among disubstituted amino radicals, symetrically substituted are usually preferred and more easily accessible.

As used herein with respect to a substituting radical, and unless otherwise stated, the terms "(thio)carboxylic acid ester", "(thio)carboxylic acid thioester" and "(thio)carboxylic acid amide" refer to radicals wherein the carboxyl or thiocarboxyl group is directly attached to the pteridine ring (e.g. in the 6- and/or 7-position) and wherein said carboxyl or thiocarboxyl group is bonded to the hydrocarbonyl residue of an alcohol, a thiol, a polyol, a phenol, a thiophenol, a primary or secondary amine, a polyamine, an aminoalcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic amino, hydroxyalkylamino, mercaptoalkylamino or alkynylamino (such as above defined, respectively).

As used herein with respect to a substituting radical, and unless otherwise stated, the term "amino-acid" refers to a radical derived from a molecule having the chemical formula $H_2N$—CHR—COOH, wherein R is the side group of atoms characterizing the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula (I) or (II) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a pteridine derivative of this invention with a suitable inorganic solvent (e.g. hydrates) or organic solvent, such as but not limited to alcohols, ketones, esters and the like.

As used herein and unless otherwise stated, the terms "dihydropteridine derivative" and "tetrahydropteridine derivative" refer to the hydrogenation products of the pteridine derivatives having formula (I) or (II), i.e. derivatives wherein two hydrogen atoms are present in positions 5 and 6, or 7 and 8, of the pteridine ring, or wherein four hydrogen atoms are present in positions 5, 6, 7 and 8 of the said ring; such hydrogenated derivatives are easily accessible from the pteridine derivatives using hydrogenation methods well known in the art.

DETAILED DESCRIPTION OF THE INVENTION

A main object of the invention is to provide a pharmaceutical composition having high immunosuppressive activity. Thus, the present invention relates in particular to the medical applications of a group of pteridine derivatives, their pharmaceutically acceptable salts, N-oxides, solvates, dihydro- and tetrahydroderivatives and enantiomers, possessing unexpectedly desirable pharmaceutical properties, in particular which are highly active immunosuppressive agents, and as such are useful in the treatment in transplant rejection and/or in the treatment of certain inflammatory diseases.

Surprisingly, the compounds of the present invention show a broader therapeutic spectrum profile than merely immunosuppressive activity, as is evidenced by the results obtained in the diversity of test procedures disclosed hereinbelow. A further advantageous feature of the compounds of the present invention resides in their excellent oral activity.

In the first embodiment of the invention, the novel pteridine derivatives are as defined in the general formula (I), wherein each of the substituents X, Z, $R_x$, $R_2$, $R_3$ and $R_4$ may correspond to any of the definitions given above (and, when X includes sulfur, wherein m may be 0, 1 or 2), in particular with any of the individual meanings (such as illustrated above) of generic terms such as, but not limited to, "$C_{1-7}$ alkyl", "$C_{2-7}$ alkenyl", "$C_{2-7}$ alkynyl", "aryl alkylaryl", "arylalkyl", "alkylamino", "cycloalkylamino", "alkenylamino", "alkynylamino", "arylamino", "arylalkylamino", "$C_{1-7}$ alkoxy", "$C_{3-10}$ cycloalkoxy", "thio $C_{1-7}$ alkyl", "thio $C_{3-10}$ cycloalkyl", "halo $C_{1-7}$ alkyl", "amino-acid" and the like.

When a mixture of enantiomers of a pteridine derivative having the general formula (I) according to the invention is obtained during synthesis, the said mixture may be separated by means and methods standard in the art, e.g. liquid chromatography using one or more suitable chiral stationary phases. The latter include, for example, polysaccharides, in particular cellulose or amylose derivatives. Commercially available polysaccharide-based chiral stationary phases suitable for this purpose are ChiralCel™ CA, OA, OB, 0C, OD, OF, OG, OJ and OK, and Chiralpak™ AD, AS, OP(+) and OT(+). Appropriate eluents or mobile phases for use in combination with said polysaccharide-based chiral stationary phases are hydrocarbons such as hexane and the like, optionally admixed with an alcohol such as ethanol, isopropanol and the like. The above mixture of enantiomers may alternatively be separated by forming diastereoisomers, followed by separation of the diastereoisomers, e.g. by differential crystallization or chromatography. The resolving agent may be cleaved from the separated diastereoisomers, e.g. by treatment with acids or bases, in order to generate the pure enantiomers of the compounds of the invention.

Some preferred pteridine derivatives having the general formula (I) or (II) according to the invention are more specifically illustrated in the following examples and defined in the following claims. For instance, useful pteridine species disclosed below include those wherein:

$R_1$ is selected from the group consisting of methyl, ethyl, isopropyl, pentyl and benzyl, and/or $R_2$ is amino, and/or $R_4$ is hydrogen or methoxy, and/or $R_3$ is 3-thienyl or a phenyl group with one or more substituents (in the latter case, such substituents are preferably each independently selected from the group consisting of fluoro, methoxy, ethoxy, trifluoromethyl, dimethylamino, chloro, cyano, methyl, ethyl, carboxymethyl, methylthio, dimethylcarboxamido, diethylcarboxamido and methylcarboxylate, and/or X is a sulfur atom (i.e. m is 0) or an oxygen atom, or X is NZ, wherein Z is selected from the group consisting of hydrogen, methyl, ethyl, isopropyl and benzyl, or NZ together with $R_1$ forms a radical selected from the group consisting of hydroxylamino, morpholinyl, piperidinyl, piperazinyl, N-methylpiperazinyl, 1,2,4-triazolyl and pyrrolidinyl.

The present invention further provides processes and methods for making the novel pteridine derivatives having the general formula (I). As a general rule, the preparation of these compounds is based on the principle that, starting from a suitable pteridine precursor, each of the substituents $XR_1$, $R_2$, $R_3$ and $R_4$ may be introduced separately (except, of course, when $R_3$ together with $R_4$ forms a homocyclic or heterocyclic radical) without adversely influencing the presence of one or more substituents already introduced at other positions on the pteridine ring or the capacity to introduce further substituents later on.

Methods of manufacture have been developed by the present inventors which may be used alternatively to, or may be combined with, the methods of synthesis already known in the art of pteridine derivatives (depending upon the targeted final compound). For instance, methods for simultaneously introducing $R_3$ and $R_4$ in the form of a homocyclic or heterocyclic radical at positions 6 and 7 of the pteridine ring are already known from U.S. Pat. No. 2,581,889. The synthesis of mono- and di-N-oxides of the pteridine derivatives of this invention can easily be achieved by treating the said derivatives with an oxidizing agent such as, but not limited to, hydrogen peroxide (e.g. in the presence of acetic acid) or a peracid such as chloroperbenzoic acid. Dihydro- and tetrahydropteridine derivatives of this invention can easily be obtained by catalytic hydrogenation of the corresponding pteridine derivatives, e.g. by placing the latter in a hydrogen atmosphere in the presence of platinum oxide or platinum. The methods for making the pteridine derivatives of the present invention will now be explained in more details by reference to the appended FIGS. 1 to 5 wherein, unless otherwise stated hereinafter, each of the substituting groups or atoms X, Z, $R_1$, $R_2$, $R_3$ and $R_4$ is as defined in formula (I) of the summary of the invention and, more specifically, may correspond to any of the individual meanings disclosed above. The same manufacturing methods may also be applied, if need be, while starting from pteridine derivatives which are already known in the art. In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

FIG. 1 represents a scheme for the preparation of 2,4,6-trisubstituted pteridines with various $R_2$ and $R_3$ substituents in the 2- and 6-positions of the pteridine ring. In the first step (a), a chloropyrimidine 1, wherein $R_2$ may be inter alia amino, alkylamino, arylamino, alkoxy, aryloxy, mercaptoalkyl, or mercaptoaryl, is reacted with an appropriate nucleophile $R_1XH$, the said nucleophile being selected from the group consisting of alcohols (e.g. methanol, ethanol, isopropanol or benzylalcohol), thiols, primary amines and secondary amines wherein $R_1$ may be inter alia alkyl, cycloalkyl, aryl, alkylaryl, heteroaryl or alkylheteroaryl. Introduction of a nitroso group into the pyrimidine intermediate 2 occurs in step (b) under acidic aqueous conditions in the presence of sodium nitrite $NaNO_2$. Reduction of the nitroso functionality of the pyrimidine intermediate 3 into a free amino group in intermediate 4 is then effected in step (c) by means of reducing agents (such as $Na_2S_2O_4$ or $(NH_4)_2S$) in water, or catalytically ($Pt/H_2$) in the presence of a protic solvent. In step (d), ring closure is performed by treating the diaminopyrimidine 4 with glyoxal in order to form a pteridine ring. In step (e), the nitrogen atom at position 8 of the pteridine ring of compound 5 is oxidized, e.g. using $H_2O_2$ under acidic conditions. In step (f), a chlorine atom is regioselectively introduced on the 6 position of the pteridine ring of compound 6 by treatment with a carboxylic acid choride such as acetyl chloride under acidic conditions. Then in step (g) the 6-chlorosubstituted pteridine 7 is reacted with a boronic acid having the general formula $R_3B(OH)_2$, wherein $R_3$ may be alkyl, cycloalkyl, aryl or heteroaryl, under basic conditions (such as in the presence of an aqueous alcaline solution) and a palladium based catalyst, thus yielding the desired derivative 8 of the present invention.

Figure 2:
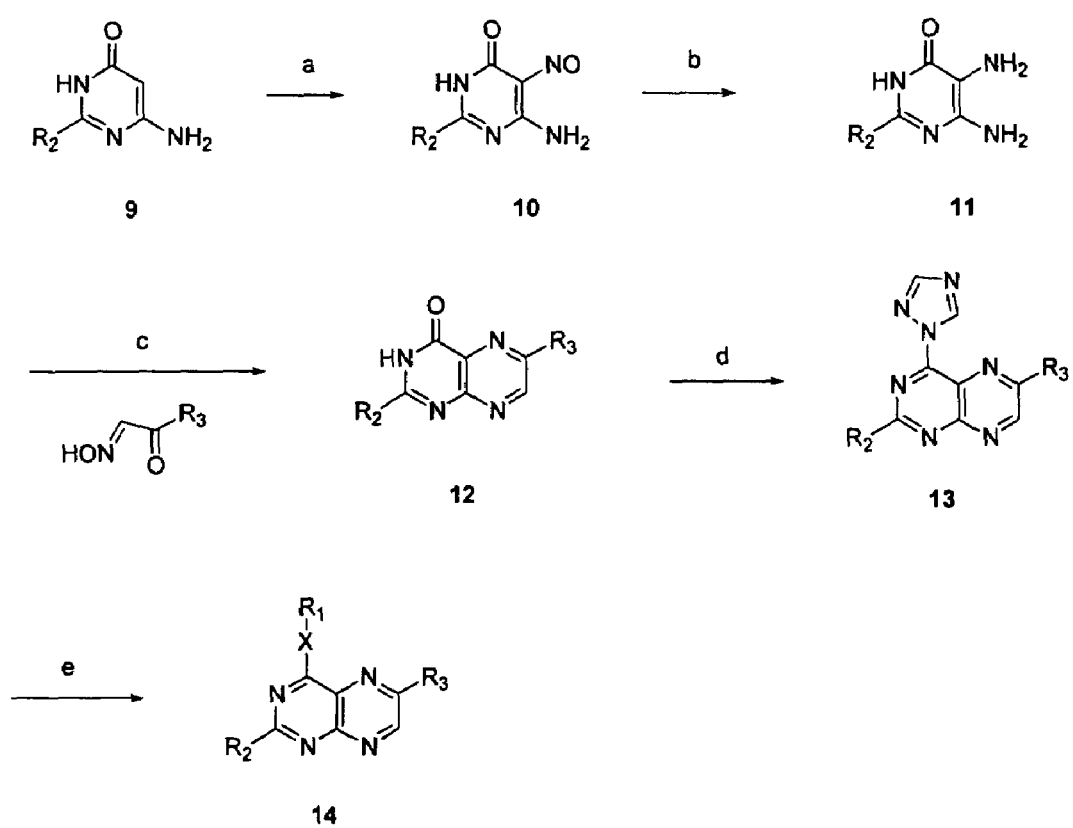

FIG. 2 represents a scheme for the preparation of 2,4,6-trisubstituted pteridines with various $R_2$ and $R_3$ substituents in the 2- and 6-positions of the pteridine ring. In step (a), a nitroso group is introduced in position 5 of the pyrimidine ring of a compound 9, wherein $R_2$ may be inter alia amino, alkylamino or arylamino, using sodium nitrite under aqueous acidic conditions. Reduction of the nitroso group of compound 10 in step (b) is achieved either catalytically ($Pt/H_2$) in the presence of a protic solvent, or chemically using sodium dithionite or ammonium sulfide in the presence of water. Then in the next step (c), the condensation of the diaminopyrimidine II with an α-ketoaldoxime bearing the group $R_3$, wherein $R_3$ may be alkyl, cycloalkyl, aryl or heteroaryl, under acidic conditions in the presence of a protic solvent such as methanol, regioselectively yields the 6-substituted pteridine derivative 12. Activation of the hydroxyl group of the tautomeric form of 12 by a nucleophilic displacement reaction occurs by preparing the 4-[(1,2,4)-triazolyl] pteridine derivative 13, using $POCl_3$ or 4-chlorophenyl phosphorodichloridate, and 1,2,4-triazole in the presence of e.g. pyridine as solvent. If $R_2$ is a free amino group, protection of $R_2$ e.g. by means of an acetyl group may be necessary before carrying out the reaction of step (d), followed by a deprotection of the acetyl group during the nucleophilic displacement reaction. The nucleophilic substitution in step (e) may be performed, e.g. in the presence of 1,4-dioxane as a solvent, by mixing the pteridine derivative 13 at room temperature with an appropriate nucleophile $R_1XH$, the said nucleophile being selected from the group consisting of alcohols (e.g. methanol, ethanol, isopropanol or benzylalcohol), thiols, primary amines and secondary amines wherein $R_x$ may be inter alia alkyl, cycloalkyl, aryl, alkylaryl, heteroaryl or alkylheteroaryl, thus yielding the desired derivative 14 of the present invention.

Figure 3:
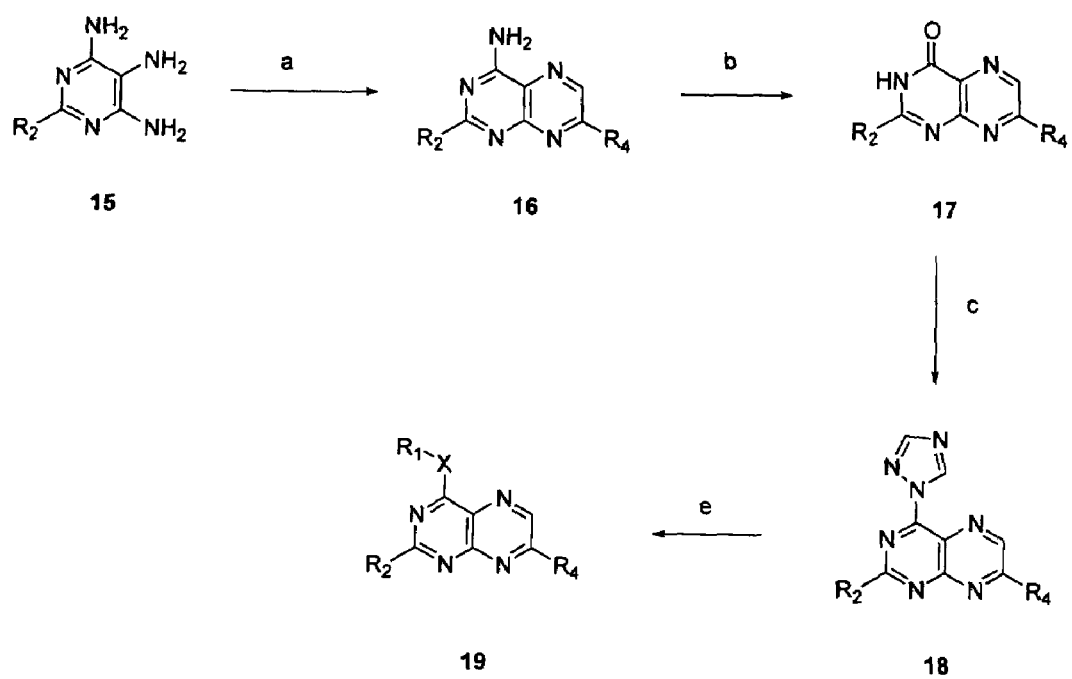
FIG. 3 represents a scheme for preparing 2,4,7-trisubstituted pteridine derivatives according to this invention.

FIG. 3 represents a scheme for the preparation of 2,4,7-trisubstituted pteridines with various $R_2$ and $R_4$ substituents in the 2- and 7-positions of the pteridine ring. In reaction step (a), a tetraminopyrimidine 15, wherein $R_2$ may be inter alia amino, alkylamino or arylamino, is reacted with inter alia an alkylglyoxal, arylglyoxal, alkylarylglyoxal, heteroarylglyoxal or alkyl heteroarylglyoxal in water under basic conditions, yielding the 7-substituted pteridine derivative 16 wherein $R_4$ may be inter alia alkyl, cycloalkyl, aryl, heteroaryl, alkylaryl or alkylheteroaryl. In step (b), hydrolysis under reflux in the presence of sodium hydroxide 1N yielded the 4-hydroxy tautomer of pteridine derivative 17. In step (c), a 1,2,4-triazolyl group is introduced in position 4 by reacting 17 with triazole in the presence of 4-chlorophenyl phosphorodichloridate and dry pyridine. Finally in reaction step (d), the 1,2,4-triazolyl group at position 4 of the pteridine derivative 18 is displaced by an appropriate nucleophie $R_1XH$, the said nucleophile being selected from the group consisting of alcohols (e.g. methanol, ethanol, isopropanol or benzylalcohol), thiols, primary amines and secondary amines wherein $R_x$ may be inter alia alkyl, cycloalkyl, aryl, alkylaryl, heteroaryl or alkylheteroaryl, in the presence of a polar aprotic or protic solvent, thus yielding the desired derivative 19 of the present invention.

Figure 4:
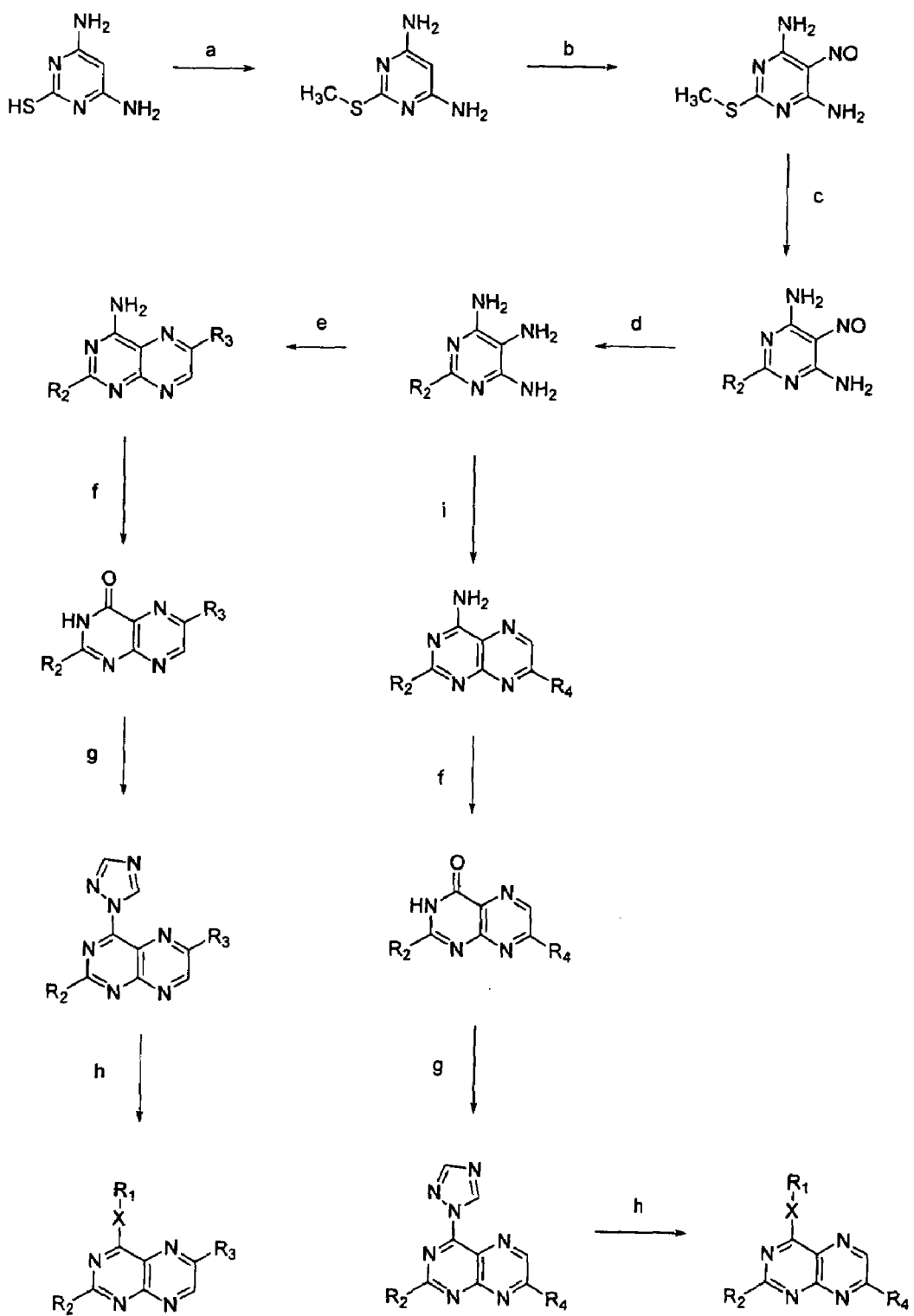
FIG. 4 represents a scheme for preparing unsymmetrical 2,4,6-trisubstituted pteridines and 2,4,7-trisubstituted pteridines according to this invention.

FIG. 4 represents a scheme for the synthesis of unsymmetrical 2,4,6-trisubstituted and 2,4,7-trisubstituted pteridine derivatives with various $R_2$, $R_3$ and $R_4$ substituents in the 2-, 6- and 7-positions of the pteridine ring. In step (a), the thiol function on 2-mercapto-4,6-diaminopyrimidine is methylated, e.g. by reaction with methyl iodide in the presence of a solvent such as ethanol, in order to yield 2-thiomethyl-4,6-diaminopyrimidine. Introduction of a nitroso group in the 5-position of the pyrimidine ring is then achieved in step (b) by using sodium nitrite under aqueous acidic conditions. In the next step (c), the methylthio group in the 2-position is exchanged for a group $R_2$, wherein $R_2$ may be inter alia alkoxy, aryloxy, cycloalkyloxy, heteroaryloxy, mercaptoalkyl, mercaptoaryl, mercaptocyclo-alkyl or mercaptoheteroaryl by reaction with an appropriate nucleophile. Reduction of the nitroso functionality is then achieved in step (d) either catalytically ($Pt/H_2$) in the presence of a protic solvent or chemically using sodium dithionite or ammonium sulfide in the presence of water. Then in the next step (e), the condensation of the 2-substituted-4,5,6-triaminopyrimidine with an α-ketoaldoxime bearing the group $R_3$, wherein $R_3$ may be inter alia alkyl, cycloalkyl, aryl or heteroaryl, under acidic conditions in the presence of a solvent such as methanol, regioselectively yields a 2,6-substituted-4-aminopteridine derivative. The corresponding 2,7-substituted-4-aminopteridine can be obtained, according to step (i), by reaction of the 2-substituted-4,5,6-triaminopyrimidine with a glyoxal bearing the group $R_4$, wherein $R_4$ may be inter alia alkyl, cycloalkyl, aryl or heteroaryl. According to step (f), acidic or basic hydrolysis of the amino group at position 4 of the pteridine ring, performed on the derivative from step (e) or (i), yields the corresponding 4-oxopteridine derivative. In step (g), the hydroxyl group of the tautomeric form of the latter is activated by nucleophilic displacement, e.g. by preparing the 4-[(1,2,4)-triazolyl] pteridine derivative. Finally, the nucleophilic displacement in step (h) is performed by mixing the said 4-triazolyl pteridine derivative with the appropriate nucleophile $R_1XH$, wherein $R_1$ may be inter alia alkyl, cycloalkyl, aryl, heteroaryl, alkylaryl, alkylheteroaryl.

Figure 5:
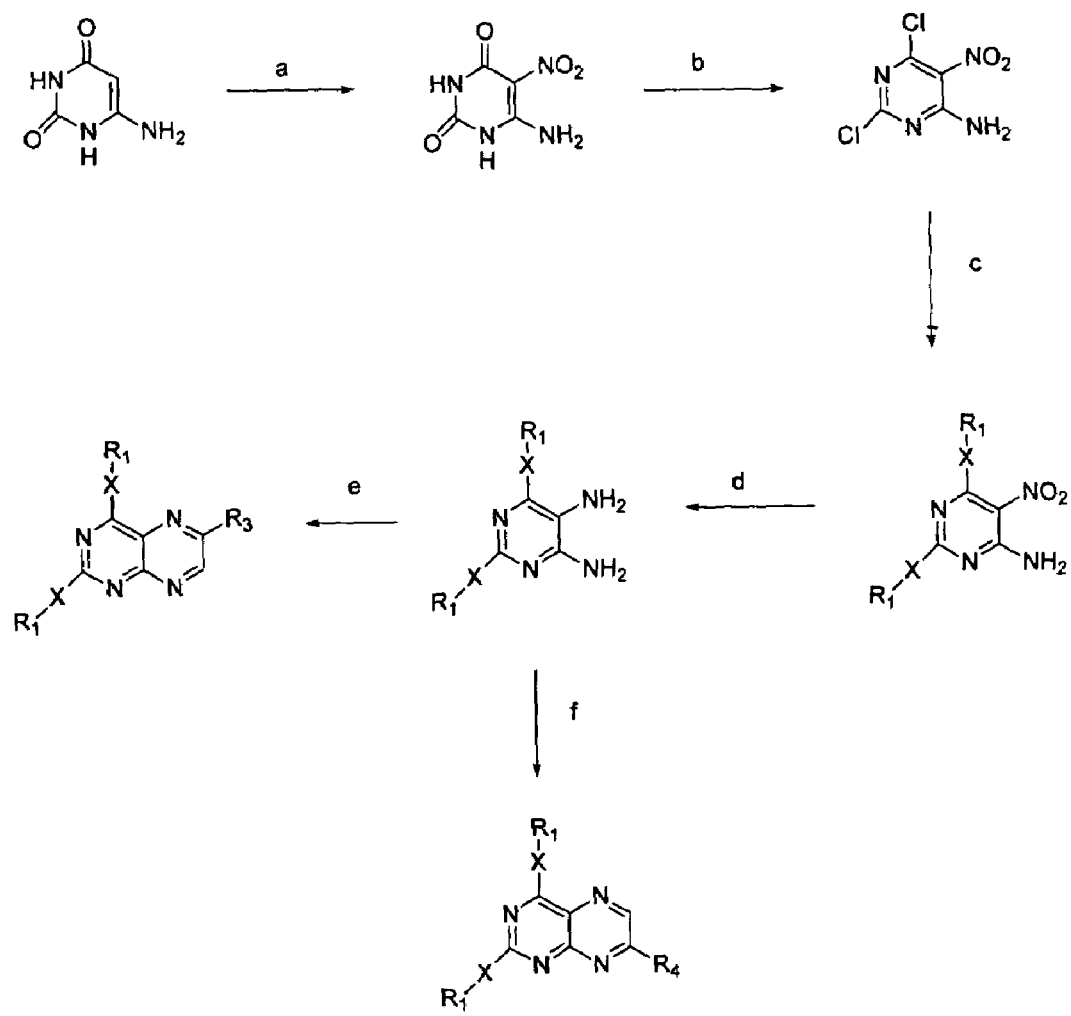
FIG. 5 represents a scheme for preparing symmetrical 2,4,6-trisubstituted pteridines and 2,4,7-trisubstituted pteridines according to this invention.

FIG. 5 represents a scheme for the synthesis of symmetrical 2,4,6-trisubstituted and 2,4,7-trisubstituted pteridine derivatives with various $R_2$, $R_3$ and $R_4$ substituents in the 2-, 6- and 7-positions of the pteridine ring. In step (a), the pyrimidine ring is nitrated in position 5 under strongly acidic conditions ($HNO_3$, $H_2SO_4$). Then in step (b) both hydroxyl groups (from the tautomeric form) are converted to chloro groups by treatment with a chlorinating agent such as $POCl_3$ or $SOCl_2$. Both chloro substituents are then displaced in step (c) with an appropriate nucleophile $R_1XH$, wherein $R_1$ may be inter alia alkyl, cycloalkyl, aryl, heteroaryl, alkylaryl, alkylheteroaryl. The nitro group is reduced in step (d) to an amino group by treatment with a reducing agent (e.g. $Pt/H_2$). Finally, reaction of the 2,4-substituted-5,6-diaminopyrimidine from step (d) with an α-ketoaldoxime bearing the group $R_3$, wherein $R_3$ may be inter alia alkyl, cycloalkyl, aryl or heteroaryl, regioselectively yields the desired 2,4,6-trisubstituted pteridine derivative in step (e). Alternatively, reaction of the 2,4-substituted-5,6-diaminopyrimidine from step (d) with a glyoxal bearing the group $R_4$, wherein $R_4$ may be inter alia alkyl, cycloalkyl, aryl or heteroaryl, yields the desired 2,4,7-trisubstituted pteridine derivative in step (f).

Some sub-sets of pteridine derivatives according to the invention deserve specific interest. Thus in a particular embodiment the invention relates to a group of pteridine derivatives, as well as pharmaceutical compositions comprising such pteridine derivatives as active principle, having the above general formula (I) wherein:

X is NZ, $XR_1$ is selected from the group consisting of hydroxylamino; hydrazino (i.e. Z is hydrogen and $R_1$ is amino); (mono- or di-) $C_{1-7}$ alkylamino (i.e. $R_1$ is $C_{1-7}$ alkyl); (mono- or di-) arylamino (i.e. $R_1$ is aryl, e.g. adamantyl); (mono- or di-) $C_{3-10}$ cycloalkylamino (i.e. $R_1$ is $C_{3-10}$ cycloalkyl); (mono- or di-) hydroxy$C_{1-7}$ alkylamino (i.e. $R_1$ is $C_{1-7}$ alkyl substituted with hydroxyl); (mono- or di-) $C_{1-4}$ alkylarylamino; and saturated or unsaturated heterocyclic groups containing at least one nitrogen atom and optionally substituted by one or more substituents independently selected from the group consisting of $C_{1-4}$ alkyl, hydroxy $C_{1-4}$ alkyl, $C_{1-4}$ alkyloxy, halogen, hydroxy, hydroxycarbonyl and $C_{14}$ alkyloxycarbonyl, such as but not limited to piperazinyl, N-alkylpiperazinyl and morpholinyl;

$R_2$ is amino or is selected from the group consisting of hydroxylamino; hydrazino (i.e. Z is hydrogen and $R_1$ is amino); (mono- or di-) arylamino (i.e. $R_1$ is aryl); (mono- or di-) $C_{3-10}$ cycloalkylamino (i.e. $R_1$ is $C_{3-10}$ cycloalkyl); (mono- or di-) hydroxy$C_{1-7}$ alkylamino (i.e. $R_1$ is $C_{1-7}$ alkyl substituted with hydroxyl); (mono- or di-) $C_{1-4}$ alkylarylamino; and saturated or unsaturated heterocyclic groups containing at least one nitrogen atom and optionally substituted by one or more substituents independently selected from the group consisting of $C_{1-4}$ alkyl, hydroxy $C_{1-4}$ alkyl, $C_{1-4}$ alkyloxy, halogen, hydroxy, hydroxycarbonyl and $C_{1-4}$ alkyloxycarbonyl, such as but not limited to piperazinyl, N-alkylpiperazinyl and morpholinyl;

$R_3$ is selected from the group consisting of unsubstituted, monosubstituted and disubstituted aryl groups (wherein the substituent(s) may independently be halogen, $C_{1-4}$ alkoxy or $C_{1-4}$ alkyl); 3,4,5-trimethoxyphenyl; 3,4-formylidene-3,4-dihydroxyphenyl; aryl groups bonded to the pteridine ring via a saturated or unsaturated aliphatic spacer which may be halogenated or hydroxylated; and aliphatic substituents which may contain ether function, alcohol function, or substituted or unsubstituted amino functions or $C_{1-4}$ alkyloxy; and $R_4$ is selected from the group consisting of hydrogen, alkyl and alkoxy;

or a pharmaceutically acceptable addition salt or a stereochemical isomeric form thereof.

In another particular embodiment, the invention relates to a group of pteridine derivatives, as well as pharmaceutical compositions comprising such pteridine derivatives as active principle, having the above general formula (I) wherein:

X is oxygen or sulfur;

$R_1$ is $C_{1-7}$ alkyl;

$R_2$ is amino or is selected from the group consisting of hydroxylamino; hydrazino (i.e. Z is hydrogen and $R_1$ is amino); (mono- or di-) arylamino (i.e. $R_1$ is aryl); (mono- or di-) $C_{3-10}$ cycloalkylamino (i.e. $R_1$ is $C_{3-10}$ cycloalkyl); (mono- or di-) hydroxy$C_{1-7}$ alkylamino (i.e. $R_1$ is $C_{1-7}$ alkyl substituted with hydroxyl); (mono- or di-) $C_{1-4}$ alkylarylamino; and saturated or unsaturated heterocyclic groups containing at least one nitrogen atom and optionally substituted by one or more substituents independently selected from the group consisting of $C_{1-4}$ alkyl, hydroxy $C_{14}$ alkyl, $C_{1-14}$ alkyloxy, halogen, hydroxy, hydroxycarbonyl and $C_{1-4}$ alkyloxycarbonyl, such as but not limited to piperazinyl, N-alkylpiperazinyl and morpholinyl;

$R_3$ is selected from the group consisting of unsubstituted, monosubstituted and disubstituted aryl groups (wherein the substituent(s) may independently be halogen, $C_{1-4}$ alkoxy or $C_{1-4}$ alkyl); aryl groups bonded to the pteridine ring via a saturated or unsaturated aliphatic spacer which may be halogenated or hydroxylated; and aliphatic substituents which may contain ether function, alcohol function, or substituted or unsubstituted amino functions or $C_{1-4}$ alkyloxy; and $R_4$ is selected from the group consisting of hydrogen, alkyl and alkoxy;

or a pharmaceutically acceptable addition salt or a stereochemical isomeric form thereof.

In another particular embodiment, the invention relates to a group of pteridine derivatives having the above general formula (I) wherein X represents an oxygen atom or a group with the formula $S(O)_m$, wherein m is an integer from 0 to 2, or a group with the formula NZ and wherein:

$R_1$ is a group selected from the group consisting of $C_{1-4}$ alkyl, $C_{2-7}$ alkenyl, $C_{2-7}$ alkynyl, $C_{3-10}$ cycloalkyl, $C_{3-10}$ cycloalkenyl, aryl, alkylaryl, arylalkyl, heterocyclic, heterocyclic-substituted alkyl and alkyl-substituted heterocyclic, each of said groups being optionally substituted with one or more substituents selected from the group consisting of halogen, $C_{1-4}$ alkyl, $C_{1-4}$ alkoxy, $C_{2-7}$ alkenyl, $C_{2-7}$ alkynyl, halo $C_{1-4}$ alkyl, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxyl, sulfhydryl, nitro, hydroxylamino, mercaptoamino, cyano, carboxylic acid or esters or thioesters or amides or thioamides or halides or anhydrides thereof, thiocarboxylic acid or esters or thioesters or amides or thioamides or halides or anhydrides thereof, carbamoyl, thiocarbamoyl, ureido, thioureido, amino, cycloalkylamino, alkenylamino, cycloalkenylamino, alkynylamino, arylamino, arylalkyl-amino, hydroxylkylamino, mercaptoalkyl-amino, heterocyclic amino, hydrazino, alkylhydrazino and phenyl-hydrazino; or $R_1$ is a carboxyalkyl, carboxyaryl, thiocarboxyaryl or thiocarboxyalkyl group;

Z is a group independently defined as $R_1$ or Z is hydrogen or the group NZ together with $R_1$ is either hydroxylamino or an optionally substituted heterocyclic group containing at least one nitrogen atom;

$R_2$ is selected from the group consisting of amino; acylamino; thioacylamino; carbamoyl; thiocarbamoyl, ureido; thio-ureido, sulfonamido; hydroxylamino; alkoxyamino; thioalkylamino; mercaptoamino, hydrazino; alkylhydrazino; phenylhydrazino; optionally substituted heterocyclic radicals; $C_{3-7}$ alkylamino; arylamino; arylalkyl-amino; cycloalkylamino; alkenylamino; cycloalkenylamino; heterocyclic amino; hydroxyalkylamino; mercaptoalkylamino; $C_{1-7}$ alkoxy; $C_{3-10}$ cycloalkoxy; thio $C_{1-7}$ alkyl; arylsulfoxide; arylsulfone; heterocyclic sulfoxide; heterocyclic sulfone; thio $C_{3-10}$ cycloalkyl; aryloxy; arylthio; arylalkyloxy; arylalkylthio; oxyheterocyclic and thioheterocyclic radicals;

$R_4$ is an atom or a group selected from the group consisting of hydrogen; halogen; $C_{1-7}$ alkyl; $C_{2-7}$ alkenyl; $C_{2-7}$ alkynyl; halo $C_{1-7}$ alkyl; carboxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; mercapto-amino; acylamino; thio-acylamino; alkoxyamino; thioalkylamino; acetal; thio-acetal; carboxylic acid; carboxylic acid esters, thioesters, halides, anhydrides, amides and thioamides; thiocarboxylic acid; thiocarboxylic acid esters, thioesters, halides, anhydrides, amides and thioamides; hydroxyl; sulfhydryl; nitro; cyano; carbamoyl; thiocarbamoyl, ureido; thio-ureido; alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters, thioesters, halides, anhydrides, amides and thioamides thereof; aryl being optionally substituted with one or more substituents selected from the group consisting of halogen, $C_{1-7}$ alkyl, $C_{1-7}$ alkoxy, $C_{2-7}$ alkenyl, $C_{2-7}$ alkynyl, halo $C_{1-7}$ alkyl, nitro, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thio-ureido, sulfonamido, hydroxylamino, alkoxyamino, mercaptoamino, thioalkylamino, acylamino, thioacyl-amino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; optionally substituted heterocyclic radicals; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), thiocarbonyl, alcohol (hydroxyl), thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid or ester or thioester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfinyl, sulfonamido and halogen; branched or straight, saturated or unsaturated aliphatic chains of 1 to 7 carbon atoms optionally containing one or more functions selected from the group consisting of carbonyl (oxo), thiocarbonyl, alcohol (hydroxyl), thiol, ether, thio-ether, acetal, thio-acetal, amino, imino, oximino, alkyloximino, aminoacid, cyano, acylamino; thioacylamino; carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfinyl, sulfonamido and halogen; and $R_3$ is selected from chloro and thiomethyl;

and/or a pharmaceutically acceptable addition salt thereof and/or a stereoisomer thereof and/or a mono- or a di-N-oxide thereof and/or a solvate and/or a dihydro- or tetrahydropteridine derivative thereof.

When applicable, and depending upon the specific substituents being present, not only the novel pteridine having the general formula (I) but also some pteridine derivatives previously known in the art without any indication of biological activity, i.e. all of the pteridines having the general formula (II) according to this invention, may be in the form of a pharmaceutically acceptable salt. The latter include any therapeutically active non-toxic addition salt which compounds having the general formula (II) are able to form with a salt-forming agent. Such addition salts may conveniently be obtained by treating the pteridine derivatives of the invention with an appropriate salt-forming acid or base. For instance, pteridine derivatives having basic properties may be converted into the corresponding therapeutically active, non-toxic acid addition salt form by treating the free base form with a suitable amount of an appropiate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutanedioic, 2-hydroxy-1,2,3-propanetricarboxylic and cyclohexanesulfamic acids and the like.

Pteridine derivatives having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the pteridine derivatives (II) of this invention with an appropriate salt-forming acid or base are similar to standard conditions involving the same acid or base but different organic compounds with basic or acidic properties, respectively. Preferably, in view of its use in a pharmaceutical composition or in the manufacture of medicament for treating specific diseases, the pharmaceutically acceptable salt will be designed, i.e. the salt-forming acid or base will be selected so as to impart greater water-solubility, lower toxicity, greater stability and/or slower dissolution rate to the pteridine derivative of this invention.

The present invention further provides the use of a pteridine derivative represented by the general formula (II), or a pharmaceutically acceptable salt or a solvate thereof, as a biologically-active ingredient, i.e. an active principle, especially as a medicine or a diagnostic agent or for the manufacture of a medicament or a diagnostic kit. In particular the said medicament may be for the prevention or treatment of a pathologic condition selected from the group consisting of:

immune disorders, in particular organ and cells transplant rejections, and autoimmune disorders, cardiovascular disorders, allergic conditions, disorders of the central nervous system, and cell proliferative disorders.

The pathologic conditions and disorders concerned by the said use, and the corresponding methods of prevention or treatment, are detailed hereinbelow. Any of the uses mentioned with respect to the present invention may be restricted to a non-medical use (e.g. in a cosmetic composition), a non-therapeutic use, a non-diagnostic use, a non-human use (e.g. in a veterinary composition), or exclusively an in-vitro use, or a use with cells remote from an animal.

The invention further relates to a pharmaceutical composition comprising:

(a) one or more pteridine represented by the general formula (II), and (b) one or more pharmaceutically acceptable carriers.

In a third embodiment, this invention provides combinations, preferably synergistic combinations, of one or more pteridine represented by the general formula (II) with one or more biologically-active drugs being preferably selected from the group consisting of immunosuppressant and/or immunomodulator drugs, antineoplastic drugs, anti-histamines, inhibitors of allergy-causative agents (anti-allergic drugs) and antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon $CI<1$, $CI=1$, or $CI>1$, respectively. As will be explained in more detail herein-below, this principle may be applied to a number of desirable effects such as, but not limited to, an activity against transplant rejection, an activity against immunosuppression or immunomodulation, an activity against allergy or an activity against cell proliferation.

For instance the present invention relates to a pharmaceutical composition or combined preparation having synergistic effects against immunosuppression or immunomodulation and containing:

(a) one or more immunosuppressant and/or immunomodulator drugs, and (b) at least one pteridine derivative represented by the general formula (II), and
(c) optionally one or more pharmaceutical excipients or pharmaceutically acceptable carriers, for simultaneous, separate or sequential use in the treatment or prevention of autoimmune disorders and/or in transplant-rejections.

Suitable immunosuppressant drugs for inclusion in the synergistic compositions or combined preparations of this invention belong to a well known therapeutic class. They are preferably selected from the group consisting of cyclosporin A, substituted xanthines (e.g. methylxanthines such as pentoxyfylline), daltroban, sirolimus, tacrolimus, rapamycin (and derivatives thereof such as defined below), leflunomide (or its main active metabolite A771726, or analogs thereof called malononitrilamides), mycophenolic acid and salts thereof (including the sodium salt marketed under the trade name Mofetil®), adrenocortical steroids, azathioprine, brequinar, gusperimus, 6-mercaptopurine, mizoribine, chloroquine, hydroxychloroquine and monoclonal antibodies with immunosuppressive properties (e.g. etanercept, infliximab or kineret). Adrenocortical steroids within the meaning of this invention mainly include glucocorticoids such as but not limited to ciprocinonide, desoxycorticisterone, fludrocortisone, flumoxonide, hydrocortisone, naflocort, procinonide, timobesone, tipredane, dexamethasone, methylprednisolone, methotrexate, prednisone, prednisolone, triamcinolone and pharmaceutically acceptable salts thereof. Rapamycin derivatives as referred herein include O-alkylated derivatives, particularly 9-deoxorapamycins, 26-dihydrorapamycins, 40-O-substituted rapamycins and 28,40-O,O-disubstituted rapamycins (as disclosed in U.S. Pat. No. 5,665,772) such as 40-O-(2-hydroxy) ethyl rapamycin—also known as SDZ-RAD-, pegylated rapamycin (as disclosed in U.S. Pat. No. 5,780,462), ethers of 7-desmethylrapamycin (as disclosed in U.S. Pat. No. 6,440,991) and polyethylene glycol esters of SDZ-RAD (as disclosed in U.S. Pat. No. 6,331,547).

Suitable immunomodulator drugs for inclusion into the synergistic immunomodulating pharmaceutical compositions or combined preparations of this invention are preferably selected from the group consisting of acemannan, amiprilose, bucillamine, dimepranol, ditiocarb sodium, imiquimod, Inosine Pranobex, interferon-β, interferon-γ, lentinan, levamisole, lisophylline, pidotimod, romurtide, platonin, procodazole, propagermanium, thymomodulin, thymopentin and ubenimex.

Synergistic activity of the pharmaceutical compositions or combined preparations of this invention against immunosuppression or immunomodulation may be readily determined by means of one or more lymphocyte activation tests. Usually activation is measured via lymphocyte proliferation. Inhibition of proliferation thus always means immunosuppression under the experimental conditions applied. There exist different stimuli for lymphocyte activation, in particular:
a) co-culture of lymphocytes of different species (mixed lymphocyte reaction, hereinafter referred as MLR) in a so-called mixed lymphocyte culture test: lymphocytes expressing different minor and major antigens of the HLA-DR type (=alloantigens) activate each other non-specifically;
b) a CD3 assay wherein there is an activation of the T-lymphocytes via an exogenously added antibody (OKT3). This antibody reacts against a CD3 molecule located on the lymphocyte membrane which has a co-stimulatory function. Interaction between OKT3 and CD3 results in T-cell activation which proceeds via the $Ca^{2+}$/calmodulin/calcineurin system and can be inhibited e.g. by cyclosporin A (hereinafter referred as CyA);
c) a CD28 assay wherein specific activation of the T-lymphocyte proceeds via an exogenously added antibody against a CD28 molecule which is also located on the lymphocyte membrane and delivers strong co-stimulatory signals. This activation is $Ca^{2+}$-independent and thus cannot be inhibited by CyA.

Determination of the immunosuppressing or immunomodulating activity of the pteridine derivatives of this invention, as well as synergistic combinations comprising them, is preferably based on the determination of one or more, preferably at least three lymphocyte activation in vitro tests, more preferably including at least one of the MLR test, CD3 assay and CD28 assay referred above. Preferably the lymphocyte activation in vitro tests used include at least two assays for two different clusters of differentiation preferably belonging to the same general type of such clusters and more preferably belonging to type I transmembrane proteins. Optionally the determination of the immunosuppressing or immunomodulating activity may be performed on the basis of other lymphocyte activation in vitro tests, for instance by performing a TNF-α assay or an IL-1 assay or an IL-6 assay or an IL-10 assay or an IL-12 assay or an assay for a cluster of differentiation belonging to a further general type of such clusters and more preferably belonging to type II transmembrane proteins such as, but not limited to, CD69, CD 71 or CD134.

The synergistic effect may be evaluated by the median effect analysis method described herein-before. Such tests may for instance, according to standard practice in the art, involve the use of equiment, such as flow cytometer, being able to separate and sort a number of cell subcategories at the end of the analysis, before these purified batches can be analysed further.

Synergistic activity of the pharmaceutical compositions of this invention in the prevention or treatment of transplant rejection may be readily determined by means of one or more leukocyte activation tests performed in a Whole Blood Assay (hereinafter referred as WBA) described for instance by Lin et al. in *Transplantation* (1997) 63:1734–1738. WBA used herein is a lymphoproliferation assay performed in vitro using lymphocytes present in the whole blood, taken from animals that were previously given the pteridine derivative, and optionally the other immunosuppressant drug, in vivo (more details are given in example 118). Hence this assay reflects the in vivo effect of substances as assessed by an in vitro read-out assay. The synergistic effect may be evaluated by the median effect analysis method described herein-before. Various organ transplantation models in animals are also available in vivo, which are strongly influenced by different immunogenicities, depending on the donor and recipient species used and depending on the nature of the transplanted organ. The survival time of transplanted organs can thus be used to measure the suppression of the immune response.

The pharmaceutical composition or combined preparation with synergistic activity against immunosuppression or immunomodulation according to this invention may contain the pteridine derivative of formula (II) over a broad content range depending on the contemplated use and the expected effect of the preparation. Generally, the pteridine derivative content of the combined preparation is within the range of 0.1 to 99.9% by weight, preferably from 1 to 99% by weight, more preferably from 5 to 95% by weight.

The invention further relates to a composition or combined preparation having synergistic effects against cell proliferation and containing:

(a) one or more antineoplastic drugs, and
(b) at least one pteridine deivative represented by the general formula (II), and
(c) optionally one or more pharmaceutical excipients or pharmaceutically acceptable carriers, for simultaneous, separate or sequential use in the treatment or prevention of cell proliferative disorders.

Suitable antineoplastic drugs for inclusion into the synergistic antiproliferative pharmaceutical compositions or combined preparations of this invention are preferably selected from the group consisting of alkaloids, alkylating agents (including but not limited to alkyl sulfonates, aziridines, ethylenimines, methylmelamines, nitrogen mustards and nitrosoureas), antibiotics, antimetabolites (including but not limited to folic acid analogs, purine analogs and pyrimidine analogs), enzymes, interferon and platinum complexes. More specific examples include acivicin; aclarubicin; acodazole; acronine; adozelesin; aldesleukin; altretamine; ambomycin; ametantrone; aminoglutethimide; amsacrine; anastrozole; anthramycin; asparaginase; asperlin; azacitidine; azetepa; azotomycin; batimastat; benzodepa; bicalutamide; bisantrene; bisnafide; bizelesin; bleomycin; brequinar; bropirimine; busulfan; cactinomycin; calusterone; caracemide; carbetimer; carboplatin; carmustine; carubicin; carzelesin; cedefingol; chlorambucil; cirolemycin; cisplatin; cladribine; crisnatol; cyclophosphamide; cytarabine; dacarbazine; dactinomycin; daunorubicin; decitabine; dexormaplatin; dezaguanine; diaziquone; docetaxel; doxorubicin; droloxifene; dromostanolone; duazomycin; edatrexate; eflornithine; elsamitrucin; enloplatin; enpromate; epipropidine; epirubicin; erbulozole; esorubicin; estramustine; etanidazole; ethiodized oil I 131; etoposide; etoprine; fadrozole; fazarabine; fenretinide; floxuridine; fludarabine; fluorouracil; flurocitabine; fosquidone; fostriecin; gemcitabine; Gold 198; hydroxyurea; idarubicin; ifosfamide; ilmofosine; interferon α-2a; interferon α-2b; interferon α-n1; interferon α-n3; interferon β-1a; interferon γ-1b; iproplatin; irinotecan; lanreotide; letrozole; leuprolide; liarozole; lometrexol; lomustine; losoxantrone; masoprocol; maytansine; mechlorethamine; megestrol; melengestrol; melphalan; menogaril; mercaptopurine; methotrexate; metoprine; meturedepa; mitindomide; mitocarcin; mitocromin; mitogillin; mitomalcin; mitomycin; mitosper; mitotane; mitoxantrone; mycophenolic acid; nocodazole; nogalamycin; ormaplatin; oxisuran; paclitaxel; pegaspargase; peliomycin; pentamustine; peplomycin; perfosfamide; pipobroman; piposulfan; piroxantrone; plicamycin; plomestane; porfimer; porfiromycin; prednimustine; procarbazine; puromycin; pyrazofurin; riboprine; rogletimide; safingol; semustine; simtrazene; sparfosate; sparsomycin; spirogermanium; spiromustine; spiroplatin; streptonigrin; streptozocin; strontium 89 chloride; sulofenur; talisomycin; taxane; taxoid; tecogalan; tegafur; teloxantrone; temoporfin; teniposide; teroxirone; testolactone; thiamiprine; thioguanine; thiotepa; tiazofurin; tirapazamine; topotecan; toremifene; trestolone; triciribine; trimetrexate; triptorelin; tubulozole; uracil mustard; uredepa; vapreotide; verteporfin; vinblastine; vincristine; vindesine; vinepidine; vinglycinate; vinleurosine; vinorelbine; vinrosidine; vinzolidine; vorozole; zeniplatin; zinostatin; zorubicin; and their pharmaceutically acceptable salts.

Other suitable anti-neoplastic compounds include 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; anti-androgens such as, but not limited to, benorterone, cioteronel, cyproterone, delmadinone, oxendolone, topterone, zanoterone and their pharmaceutically acceptable salts; anti-estrogens such as, but not limited to, clomethrone; delmadinone; nafoxidine; nitromifene; raloxifene; tamoxifen; toremifene; trioxifene and their pharmaceutically acceptable salts; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin; azasetron; azatoxin; azatyrosine; baccatin III derivatives; balanol; batimastat; BCR/ABL antagonists; benzochlorins; benzoylstaurosporine; β-lactam derivatives; β-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis-porphyrin; clomifene and analogues thereof; clotrimazole; collismycin A and B; combretastatin and analogues thereof; conagenin; crambescidin 816; cryptophycin and derivatives thereof; curacin A; cyclopentanthraquinones; cycloplatam; cypemycin; cytarabine; cytolytic factor; cytostatin; dacliximab; dehydrodidemnin B; deslorelin; dexifosfamide; dexrazoxane; dexverapamil; didemnin B; didox; diethylnorspermine; dihydro-5-azacytidine; dihydrotaxol; dioxamycin; diphenyl spiromustine; docosanol; dolasetron; doxifluridine; droloxifene; dronabinol; duocarmycin SA; ebselen; ecomustine; edelfosine; edrecolomab; elemene; emitefur; epristeride; estrogen agonists and antagonists; exemestane; filgrastim; finasteride; flavopiridol; flezelastine; fluasterone; fluorodaunorunicin; forfenimex; formestane; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idoxifene; idramantone; ilomastat; imidazoacridones; imiquimod; immunostimulant peptides; insulin-like growth factor-1 receptor inhibitor; interferon agonists; iobenguane; iododoxorubicin; ipomeanol; irinotecan; iroplact; irsogladine; isobengazole; isohomohalicondrin B; itasetron; jasplakinolide; kahalalide F; lamellarin-N; leinamycin; lenograstim; lentinan; leptoistatin; leukemia inhibiting factor; leuprorelin; levamisole; liarozole; lissoclinamide; lobaplatin; lombricine; lonidamine; lovastatin; loxoribine; lurtotecan; lutetium texaphyrin; lysofylline; mannostatin A; marimastat; masoprocol; maspin; matrilysin inhibitors; matrix metalloproteinase inhibitors; merbarone; meterelin; methioninase; metoclopramide; MIF inhibitors; mifepristone; miltefosine; mirimostim; mitoguazone; mitolactol; mitonafide; mitotoxin fibroblast growth factor-saporin; mofarotene; molgramostim; human chorionic gonadotrophin monoclonal antibody; mopidamol; mycaperoxide B; myriaporone; N-acetyldinaline; N-substituted benzamides; nafarelin; nagrestip; naloxone; pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; octreotide; okicenone; onapristone; ondansetron; ondansetron; oracin; osaterone; oxaliplatin; oxaunomycin; palauamine; palmitoylrhizoxin; pamidronic acid; panaxytriol; panomifene; parabactin; pazelliptine; peldesine; pentosan; pentostatin; pentrozole; perflubron; perillyl alcohol; phenazinomycin; phenylacetate; phosphatase inhibitors; picibanil; pilocarpine; pirarubicin; piritrexim; placetin A and B; plasminogen activator inhibitor; propyl bis-acridone; prostaglandin J2; proteasome inhibitors; protein kinase C inhibitors; protein tyrosine phosphatase inhibitors; purine nucleoside phosphorylase inhibitors; purpurins; pyrazoloacridine; raltitrexed; ramosetron; ras farnesyl protein transferase inhibitors; ras inhibitors; ras-GAP inhibitors; retelliptine; rhenium 186 etidronate; rhizoxin; retinamide; rohitukine; romurtide; roquinimex; rubiginone B1; ruboxyl; saintopin; sarcophytol A; sargramostim; sizofiran; sobuzoxane; sodium borocaptate; sodium phenylacetate; solverol; somatomedin binding protein; sonermin; sparfosic acid; spicamycin D; splenopentin; spongistatin 1; squalamine; stem-cell division inhibitors; stipiamide; stromelysin inhibitors; sulfinosine; suradista; suramin; swainsonine; tallimustine; tamoxifen; tauromustine; tazarotene; tecogalan; tellurapyrylium; telomerase inhibitors; temozolomide; tetrachlorodecaoxide; tetrazomine; thaliblastine; thiocoraline; thrombopoietin; thymalfasin; thymopoietin receptor agonist; thymotrinan; thyroid stimulating hormone; tin ethyl etiopurpurin; titanocene; topsentin; tretinoin; triacetyluridine; tropisetron; turosteride; tyrosine kinase inhibitors; tyrphostins; ubenimex; urogenital sinusderived growth inhibitory factor; urokinase receptor antagonists; variolin B; velaresol; veramine; verdins; verteporfin; vinxaltine; vitaxin; zanoterone; zilascorb; and their pharmaceutically acceptable salts.

Synergistic activity of the pharmaceutical compositions or combined preparations of this invention against cell proliferation may be readily determined by means of one or more tests such as, but not limited to, the measurement of the radioactivity resulting from the incorporation of $^3$H-thymidine in culture of tumor cell lines. For instance, different tumor cell lines are selected in order to evaluate the antitumor effects of the test compounds, such as but not limited to:

RPMI1788: human Peripheral Blood Leucocytes (PBL) Caucasian tumor line,
Jurkat: human acute T cell leukemia,
EL4: C57Bl/6 mouse lymphoma, or
THP-1: human monocyte tumor line.

Depending on the selected tumor cell line, different culture media may be used, such as for example:

for RPMI1788 and THP-1: RPMI-1640+10% FCS+1% NEM+1% sodium pyruvate+5×10$^{-5}$ mercapto-ethanol+antibiotics (G-418 0.45 µ/ml).

for Jurkat and EL4: RPMI-1640+10% FCS+antibiotics (G-418 0.45 µg/ml).

In a specific embodiment of the synergy determination test, the tumor cell lines are harvested and a suspension of 0.27×10$^6$ cells/ml in whole medium is prepared. The suspensions (150 µl) are added to a microtiter plate in triplicate. Either complete medium (controls) or the test compounds at the test concentrations (50 µl) are added to the cell suspension in the microtiter plate. The cells are incubated at 37° C. under 5% CO$_2$ for about 16 hours. $^3$H-thymidine is added, and the cells incubated for another 8 hours. The cells are harvested and radioactivity is measured in counts per minute (CPM) in a β-counter. The $^3$H-thymidine cell content, and thus the measured radioactivity, is proportional to the proliferation of the cell lines. The synergistic effect is evaluated by the median effect analysis method as disclosed hereinbefore.

The pharmaceutical composition or combined preparation with synergistic activity against cell proliferation according to this invention may contain the pteridine compound of formula (II) over a broad content range depending on the contemplated use and the expected effect of the preparation. Generally, the pteridine content of the combined preparation is within the range of 0.1 to 99.9% by weight, preferably from 1 to 99% by weight, more preferably from 5 to 95% by weight.

The invention further relates to a pharmaceutical composition or combined preparation having synergistic effects against a viral infection and containing:

(a) one or more anti-viral agents, and
(b) at least one pteridine derivative represented by the general formula (II), and
(c) optionally one or more pharmaceutical excipients or pharmaceutically acceptable carriers, for simultaneous, separate or sequential use in the treatment or prevention of a viral infection.

Suitable anti-viral agents for inclusion into the synergistic anti-viral compositions or combined preparations of this invention include, for instance, retroviral enzyme inhibitors belonging to categories well known in the art, such as HIV-1 1N inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of viruses selected from the group consisting of picorna-, toga-, bunya, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV).Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477–488 and by Baba et al. in *Antimicrob. Agents Chemother.* (1984) 25:515–517, using EC$_{50}$ for calculating the fractional inhibitory concentration (hereinafter referred as FIC). When the minimum FIC index corresponding to the FIC of combined compounds (e.g., FIC$_x$+FIC$_y$) is equal to 1.0, the combination is said to be additive; when it is beween 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection according to this invention may contain the pteridine compound of formula (II) over a broad content range depending on the contemplated use and the expected effect of the preparation. Generally, the pteridine content of the combined preparation is within the range of 0.1 to 99.9% by weight, preferably from 1 to 99% by weight, more preferably from 5 to 95% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperiteneously) is also applicable as a mode of administration, for instance in the form of injectable solutions or dispersions, depending upon the disorder to be treated and the condition of the patient.

Auto-immune disorders to be prevented or treated by the pharmaceutical compositions or combined preparations of this invention include both systemic auto-immune diseases such as but not limited to lupus erythematosus, psoriasis, vasculitis, polymyositis, scleroderma, multiple sclerosis, ankylosing spondilytis, rheumatoid arthritis and Sjögren syndrome; auto-immune endocrine disorders such as thyroiditis; and organ-specific auto-immune diseases such as but not limited to Addison disease, hemolytic or pernicious anemia, Goodpasture syndrome, Graves disease, idiopathic thrombocytopenic purpura, insulin-dependent diabetes mellitus, juvenile diabetes, uveitis, Crohn's disease, ulcerative colitis, pemphigus, atopic dermatitis, autoimmune hepatitis, primary biliary cirrhosis, auto-immune pneumonitis, autoimmune carditis, myasthenia gravis, glomerulonephritis and spontaneous infertility.

Transplant rejections to be prevented or treated by the pharmaceutical compositions or combined preparations of this invention include the rejection of transplanted or grafted organs or cells (both allografts and xenografts), such as but not limited to host versus graft reaction disease. The term "organ" as used herein means all organs or parts of organs in mammals, in particular humans, such as but not limited to kidney, lung, bone marrow, hair, cornea, eye (vitreous), heart, heart valve, liver, pancreas, blood vessel, skin, muscle, bone, intestine or stomach. "Rejection" as used herein mean all reactions of the recipient body or of the transplanted organ which in the end lead to cell or tissue death in the transplanted organ or adversely affect the functional ability and viability of the transplanted organ or the recipient. In particular, this means acute and chronic rejection reactions. Also included in this invention is preventing or treating the rejection of cell transplants and xenotransplantation. The major hurdle for xenotransplantation is that even before the T lymphocytes, responsible for the rejection of allografts, are activated, the innate immune system, especially T-independent B lymphocytes and macrophages are activated. This provokes two types of severe and early acute rejection called hyper-acute rejection and vascular rejection, respectively. The present invention addresses the problem that conventional immunosuppressant drugs like cyclosporin A are ineffective in xenotransplantation. The ability of the compounds of this invention to suppress T-independent xeno-antibody production as well as macrophage activation may be evaluated in the ability to prevent xenograft rejection in athymic, T-deficient mice receiving xenogenic hamster-heart grafts.

Cell proliferative disorders to be prevented or treated by the pharmaceutical compositions or combined preparations of this invention include any kind of tumor progression or invasion or metastasis inhibition of a cancer, preferably one selected from the group consisting of lung cancer, leukaemia, ovarian cancer, sarcoma, Kaposi's sarcoma, meningioma, colon cancer, lymp node tumor, glioblastoma multiforme, prostate cancer or skin carcinose.

CNS disorders to be prevented or treated by the pharmaceutical compositions of this invention include cognitive pathologies such as dementia, cerebral ischemia, trauma, epilepsy, schizophrenia, chronic pain and neurologic disorders such as but not limited to depression, social phobia and obsessive compulsive disorders.

Cardiovascular disorders to be prevented or treated by the pharmaceutical compositions of this invention include ischemic disorders, infarct or reperfusion damage, atherosclerosis and stroke.

Allergic conditions to be prevented or treated by the pharmaceutical compositions of this invention include those caused by the pollen of graminae, the presence of pets, as well as more severe forms, such as asthma, characterized by inflammation of airways and bronchospasm. Without wishing to be bound by theory, the antiallergic effect of the compounds of the invention may be related to their suppression of certain B-cell activation pathways, which can lead to the suppression of IgE release. It may also be related to their properties of inhibiting certain Th2 cytokines, such as IL-5, IL-13 or IL-10, involved in asthma.

The term "pharmaceutically acceptable carrier or excipient" as used herein in relation to pharmaceutical compositions and combined preparations means any material or substance with which the active principle, i.e. the pteridine derivative of formula (II), and optionally the immunosuppressant or immunomodulator or antineoplastic drug or antiviral agent, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the pteridine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 μm, namely for the manufacture of microcapsules for controlled or sustained release of the biologically active ingredient(s).

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$–$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenolpolyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$–$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Since, in the case of combined preparations including the pteridine derivative of this invention and an immunosuppressant or immunomodulator or antihistamine or antineoplastic drug or antiviral agent, both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for preventing or treating a disease selected from the group consisting of CNS disorders, cell proliferative disorders, allergic conditions, viral infections, immune and auto-immune disorders and transplant rejections in a subject or patient by administering to the patient in need thereof an effective amount of a pteridine derivative having the general formula (II), optionally together with an effective amount of another immunosuppressant or immunomodulator or antineoplastic drug or antiviral agent, or a pharmaceutical composition such as disclosed above in extensive details. The effective amount is usually in the range of 0.01 mg to 20 mg, preferably 0.1 mg to 5 mg, per day per kg bodyweight for humans. Depending upon the pathologic condition to be treated and the patient's condition, the said effective amount may be divided into several subunits per day or may be administered at more than one day intervals. The patient to be treated may be any warm-blooded animal, preferably a human being, suffering from said pathologic condition.

The following examples are intended to illustrate and not to limit the scope of the present invention in all its aspects.

EXAMPLE 1

Preparation of 2-amino-4-n-pentyloxy-6-styrylpteridine

A mixture of 1.5 g (5.6 mmoles) 2-amino-6-chloro-4-n-pentyloxypteridine (e.g. available following the procedure disclosed by Mohr et al. in *Helv. Chem. Acta* (1992) 75:2317), palladium acetate (63 mg, 0.28 mmoles), tri-o-tolylphosphane (682 mg, 2.24 mmoles), cuprous iodide (53 mg, 0.28 mmoles), styrene (1,3 ml., 11.3 mmoles) and triethylamine 3.1 ml, 22 mmoles) was stirred in dry acetonitrile (50 ml) under reflux for 90 hours. It was evaporated and the residue purified by silica gel column chromatography with chloroform. The product fraction was evaporated to give 1.37 g (yield: 72%) of an orange powder exhibiting, after recrystallization from a EtOAc/hexane mixture, a melting point (m.p.) range of 127–128° C.

EXAMPLE 2

Preparation of 2-amino-6-(1,2-dibromophenethyl)-4-n-pentyloxy-pteridine

To a solution of the derivative of example 1 (1.0 g, 2.94 mmoles) in chloroform (50 ml) was added a 2 M bromine solution in chloroform (2.2 ml., 4.4 mmoles) and then the mixture was stirred at room temperature for 7 hours. It was diluted with chloroform (50 ml), washed with a saturated aqueous $Na_2SO_3$ solution (100 ml) and dried over sodium sulfate. After evaporation of the solvents, the residue was treated with toluene, filtered, washed with ether and dried in a vacuum desiccator to give 0.84 g (yield: 57%) of a yellow powder.

EXAMPLE 3

Preparation of 2-amino-4,7-dimethoxy-6-styrylpteridine

A suspension of the derivative of example 2 (0.3 g, 0.6 mmoles) is methanol (10 ml) was treated with 1 M methanolic sodium methoxide (3 ml, 3 mmoles) and then refluxed for 4 hours. It was diluted with chloroform (100 ml), washed with a saturated aqueous ammonium chloride solution and water and then the solution was dried over sodium sulfate. The filtrate was evaporated and the residue was purified by silica gel column chromatography while using chloroform as the eluent. The product fraction was evaporated to give 50 mg (yield: 26%) of a yellow powder with a melting point range of 197–198° C.

EXAMPLE 4

Preparation of $O^4$-methyl-biopterin (2-amino-4-methoxy-6-(1,2-dihydroxypropyl)pteridine)

To a solution of $N^2$, 1', 2'-O-triacetyl-biopterin (1,0 g, 2.75 mmoles), triphenyl-phosphane (12,08 g, 4.13 mmoles) and methanol (0.15 ml, 3.7 mmoles) in dry dioxane (30 ml) was added diisopropyl azodicarboxylate (0.81 g, 4.1 mmoles). After stirring for 1.5 hour at room temperature, the mixture was evaporated to dryness. The residue was purified by silica gel column chromatography while using an ethylacetate/$CHCl_3$ (1:4) mixture as the eluent. The product fraction was evaporated and dried in vacuum to give 0.4 g (yield: 38%) of $N^2$, 1',2'-O-triacetyl-$O^4$-methylbiopterin. Deacetylation of this reaction product (0.28 g, 0.74 mmole) was done by stirring it in absolute methanol (20 ml) and triethylamine (4 ml) for 24 hours. Evaporation to dryness, treatment of the residue with ether, filtration and drying gave 0.172 g (yield: 83%) of $O^4$-methyl-biopterin with a melting point range of 160–161° C.

EXAMPLE 5

Preparation of 2-amino-4-hydroxylamino-6-phenylpteridine

A suspension of 2,5,6-triamino-4-methoxypyrimidine dihydrochloride (1 g, 4 mmoles) in methanol (40 ml) was heated to boiling and then a solution of phenylglyoxalmonoxime (1 g, 6.6 mmoles) in methanol (10 ml) was added dropwise. A clear solution is obtained from which on reflux for 2 hours a precipitate was separated out. The solid (hydrochloride salt) was filtered off, suspended in water (30 ml) and then neutralized to pH 8 by concentrated ammonia. The resulting precipitate was collected, washed with water and ethanol and dried at 100° C. to give 0.84 g of a yellow powder (yield: 82%).

EXAMPLES 6 TO 53

Synthesis of 2-amino-4-dialkylamino-6-arylpteridines, 2-amino-4-di(arylalkyl)amino-6-arylpteridines, 2-amino-4-alkylamino-6-arylpterdines, 2-amino-4-(N-containing heterocyclic amino)-6-arylpteridines and 2-amino-4-alkoxy-6-arylpteridines The procedure for the synthesis of the following 2-amino-4-dialkylamino-6-arylpteridines, 2-amino-4-dialkylamino-6-arylpteridines, 2-amino-4-alkylamino6-arylpteridines, 2-amino-4-(N-containing heterocyclic amino)-6-arylpteridines and 2-amino-4-alkoxy-6-arylpteridines proceeds in three steps:
a) a solution of 2,6-diamino-4-chloro-5-p-chlorophenylazopyrimidine (a compound known from British Patent No. 677,342) (5.0 g, 16.6 mmoles) in DMF (50 ml) and 0.12 mole of the appropriate reactant, being selected from the group consisting of secondary alkylamines and arylalkylamines (e.g. dimethyl-amine in ethanol (50%), diethylamine, di-n-propylamine or dibenzylamine), primary amines (e.g. an adamantanamine), heterocyclic amines (e.g. morpholine, piperidine, pyrrolidine, piperazine or N-methylpiperazine) and alcaline metal alkoxides (e.g. sodium ethoxide or sodium isopropoxide), were heated in an oil bath at 70° C. for 5 hours. Then water (50 ml) was added, cooled and the yellow precipitate collected, washed with water and dried. Recrystallization from ethanol or a DMF/water mixture provided the relevant 2,6-diamino-4-dialkylamino-5-p-chlorophenylazopyrimidine, 2,6-diamino-4-di(arylalkyl)amino-5-p-chlorophenylazopyrimidine, 2,6-diamino-4-alkyl-amino-5-p-chlorophenylazopyrimidine, 2,6-diamino4-(N-containing hetero-cyclic amino)-5-p-chlorophenylazopyrimidine or 2,6-diamino-4-alkoxy-5-p-chlorophenylazopyrimidine with a yield ranging from 55 to 90%.
b) a suspension of the pyrimidine compound (3.28 g, 10 mmoles) resulting from step (a) in methanol (70 ml) and concentrated ammonia (10 ml) was reduced in a shaking apparatus under a hydrogen atmosphere in the presence of a Raney nickel catalyst (3.5 g) for 2 days. The catalyst was filtered off under argon atmosphere and then the filtrate evaporated in vacuo to dryness. The residue was treated with ether to remove p-chloroaniline, filtered and then the solid stirred in methanolic HCl (10%, 50 ml) overnight. The dihydrochloride salt (obtained with a yield ranging from 85 to 90%) of the relevant 2,5,6-triamino-4-dialkylaminopyrimidine, 2,5,6-triamino-4-alkoxypyrimidine, 2,5,6-triamino-4-di(arylalkyl)aminopyrimidine, 2,5,6-triamino-4-alkylaminopyrimidine or 2,5,6-triamino-4-(N-containing heterocyclic amino) pyrimidine, was collected and dried in a vacuum desiccator over KOH.
c) to a boiling solution of the 2,5,6-triamino-4-substituted pyrimidine dihydrochloride salt (5 mmoles) from step (b) in methanol (20 ml) was added a solution of the relevant arylglyoxalmonoxime (7.5 mmoles) in methanol (10 ml) dropwise and then the mixture was heated under reflux for 3 hours. After cooling, the suspension or solution was made alkaline by means of concentrated ammonia up to pH 9 and the resulting precipitate was filtered off, washed with water and dried. Recrystallization was done from ethanol and a DMF/water mixture, respectively, such as to provide a yellow solid with a yield ranging from 50 to 85%.

The following compounds were prepared according to the above general procedure:
2-amino-4-dimethylamino-6-phenylpteridine (example 6);
2-amino-4-dimethylamino-6-(4-tolyl) pteridine (example 7);
2-amino-4-dimethylamino-6-(4-methoxyphenyl)pteridine (example 8);
2-amino-4-diethylamino-6-phenylpteridine (example 9);
2-amino-4-diethylamino-6-(4-chlorophenyl)pteridine (example 10);
2-amino-4-diethylamino-6-(4-methoxyphenyl)pteridine (example 11);
2-amino-4-diethylamino-6-(3,4-dimethoxyphenyl)pteridine (example 12);
2-amino-4-dibenzylamino-6-phenylpteridine (example 13);
2-amino-4-dibenzylamino-6-(4-chlorophenyl)pteridine (example 14);
2-amino-4-dibenzylamino-6-(4-methoxyphenyl)pteridine (example 15);
2-amino-4-dibenzylamino-6-(3,4-dimethoxyphenyl)pteridine (example 16);
2-amino-4-dipropylamino-6-phenylpteridine (example 17);
2-amino-4-dipropylamino-6-(4-chlorophenyl)pteridine (example 18);
2-amino-4-dipropylamino-6-(4-methoxyphenyl)pteridine (example 19);
2-amino-4-dipropylamino-6-(3,4-dimethoxyphenyl)pteridine (example 20);
2-amino-4-morpholino-6-phenylpteridine (example 21);
2-amino-4-morpholino-6-(4-chlorophenyl)pteridine (example 22);
2-amino-4-morpholino-6-(4-methoxyphenyl)pteridine (example 23);
2-amino-4-morpholino-6-(3,4-dimethoxyphenyl)pteridine (example 24);
2-amino-4-piperidino-6-phenylpteridine (example 25);
2-amino-4-piperidino-6-(4-chlorophenyl)pteridine (example 26);
2-amino-4-piperidino-6-(4-methoxyphenyl)pteridine (example 27);
2-amino-4-piperidino-6-(3,4-dimethoxyphenyl)pteridine (example 28);

2-amino-4-N-methylpiperazino-6-phenylpteridine (example 29);
2-amino-4-N-methylpiperazino-6-(4-chlorophenyl)pteridine (example 30);
2-amino-4-N-methylpiperazino-6-(4-methoxyphenyl) pteridine (example 31);
2-amino-4-methylpiperazino-6-(3,4-dimethoxyphenyl) pteridine (example 32);
2-amino-4-pyrrolidino-6-(4-methoxyphenyl) pteridine (example 33);
2-amino-4-piperazino-6-phenylpteridine (example 34);
2-amino-4-piperazino-6-(4-chlorophenyl) pteridine (example 35);
2-amino-4-piperazino-6-(4-methoxyphenyl) pteridine (example 36);
2-amino-4-piperazino-6-(3,4-dimethoxyphenyl) pteridine (example 37);
2-amino-4-dibenzylamino-6-(3,4,5-trimethoxyphenyl) pteridine (example 38);
2-amino-4-morpholino-6-(3, 4, 5-trimethoxyphenyl) pteridine (example 39);
2-amino-4-(3-adamantylamino)-6-(3,4,5-trimethoxyphenyl) pteridine (example 40);
2-amino-4-(3-adamantylamino)-6-naphtylpteridine (example 41);
2-amino-4-(4-adamantylamino)-6-(3,4,5-trimethoxyphenyl) pteridine (example 42);
2-amino-4-(4-adamantylamino)-6-naphtylpteridine (example 43);
2-amino-4-morpholino-6-(3,4-formylidene-3,4-dihydroxyphenyl)pteridine (example 44);
2-amino-4-dimethylamino-6-(3,4-formylidene-3,4-dihydroxyphenyl)pteridine (example 45);
2-amino-4-pyrrolidino-6-(3,4-dimethoxyphenyl) pteridine (example 46);
2-amino-4-dimethylamino-6-(3,4-dimethoxyphenyl) pteridine (example 47);
2-amino-4-dimethylamino-6-methylpteridine (example 48);
2-amino-4-ethoxy-6-phenylpteridine (example 49);
2-amino-4-propylamino-6-phenylpteridine (example 50);
2-amino-4-propylamino-6-(3,4-dimethoxyphenyl) pteridine (example 51);
2-acetamido-4-isopropoxy-6-(3,4-dimethoxyphenyl) pteridine (example 52); and
2-amino-4-ethoxy-6-(3,4-dimethoxyphenyl)pteridine (example 53);

EXAMPLE 54

Synthesis of 2,6-diamino-4-ethoxy-pyrimidine

To a solution of sodium (1.05 g) in ethanol (50 ml) was added 4-chloro-2,6-diaminopyrimidine (6 g, 41.4 mmoles). The resulting solution was heated in a reactor for 6 hours at 160° C. The reaction mixture was cooled down and the precipitated sodium chloride was filtered off. The filtrate was concentrated and precipitated from ethanol (two times), affording the pure title compound as a white solid (4.53 g, 72% yield). The spectral data are identical to those described e.g. by W. Pfleiderer et al. in Chem. Ber. (1961) 94, 12.

EXAMPLE 55

Synthesis of 2,6-diamino-4-isopropoxy-pyrimidine

The same procedure as in example 54 was followed using isopropanol instead of ethanol. The filtrate was pure enough for further reaction without purification. The spectral data are identical to those described e.g. by W. Pfleiderer et al. in Chem. Ber. (1961) 94, 12.

EXAMPLE 56

Synthesis of 5-nitroso-2,6-diamino-4-ethoxy-pyrimidine

To a solution of the compound of example 54 (6.13 g, 39.8 mmoles) in 20% aqueous acetic acid (57 ml) was added dropwise a solution of $NaNO_2$ (3.29 g) in water (13 ml) at 80° C. A pink precipitate was formed which was stirred at 80° C. for an additional 2 hours. The reaction mixture was cooled down in the refrigerator overnight and the resulting precipitate was filtered off, yielding the title compound as a pink powder (4.98 g, yield 68%). Spectral data are identical with those described e.g. by W. Pfleiderer et al. in Chem. Ber. (1961) 94, 12.

EXAMPLE 57

Synthesis of 5-nitroso-2,6-diamino-4-isopropoxy-Pyrimidine

The same procedure was followed as in example 56 but starting from the compound of example 55. The product has identical spectral data to those described by W. Pfleiderer et al. (cited supra).

EXAMPLE 58

Synthesis of 2,5,6-triamino-4-ethoxy-pyrimidine

To a suspension of the compound of example 56 (7.12 g, 38.9 mmoles) in water (150 ml) at 60° C. was added sodium dithionite (46.7 mmol, 8.12 g). Additional sodium dithionite was added till the pink colour completely disappeared and a yellow solution was formed. The solution was stirred at 60° C. for another 4 hours. Water was evaporated and the resulting residue was precipitated from a small amount of water, providing the title compound as a yellow powder (4.02 g, yield 61%). Spectral data are identical with literature data (W. Pfleiderer et al. cited supra).

EXAMPLE 59

Synthesis of 2,5,6-triamino-4-isopropoxy-pyrimidine

The procedure of example 58 was followed, however using the compound of example 57 as the starting material. The spectral data of the product obtained are identical with the literature data (W. Pfleiderer et al. cited supra).

EXAMPLE 60

Synthesis of 2-amino-4-ethoxy-pteridin

To a solution of 2,5,6-triamino-4-ethoxy-pyrimidine (10.54 g, 62.37 mmoles) in ethanol (160 ml) was added glyoxal (40% solution in water, 2.7 ml, 18.6 mmoles). The reaction mixture was refluxed for 4 hours. Some insoluble material was filtered off. The filtrate was concentrated in vacuo and the residue purified by flash chromatography (silica, using a $CH_3OH/CH_2Cl_2$ mixture (5:95) as the eluent), providing the pure title compound (7.34 g, yield: 62%). The spectral data of the product are identical with the literature data (W. Pfleiderer et al. cited supra).

EXAMPLE 61

Synthesis of 2-amino-4-isopropoxy-pteridin

The procedure of example 60 was repeated, however using isopropanol as the solvent instead of ethanol. The spectral data of the product obtained are identical with the literature data (W. Pfleiderer et al. cited supra).

EXAMPLE 62

Synthesis of 2-amino-4-ethoxypteridine-N-oxide

To a cooled (0° C.) solution of the compound of example 60 (2.47 g, 12.9 mmoles) in trifluoroacetic acid (53 ml) was added dropwise 2.53 ml of a 35% aqueous $H_2O_2$ solution. The reaction mixture was kept at 4° C. for two days in the refrigerator, whereby another 1.25 ml of the same $H_2O_2$ solution was added after 1 day. The solution was concentrated in vacuo. The residue was suspended in water and neutralized by the addition of a concentrated ammonia solution. Evaporation of the solvent in vacuo and purification of the residue by flash chromatography (silica, using a $CH_3OH/CH_2Cl_2$ mixture (6:94) as the eluent) provided the title compound as a yellow powder (861 mg, yield: 32%). Mass spectrum data are as follows: m/z (%): 230 ([M+Na]$^+$, 30), 208 ([M+H]$^+$, 100), 180 [(M+H-ethene)$^+$, 10].

EXAMPLE 63

Synthesis of 2-amino-4-isopropoxypteridine-$N^8$-oxide

The procedure as described in example 62 was followed, however using the compound of example 61 as the starting material. Mass spectrum data are as follows: m/z (%): 222 ([M+H]$^+$, 100), 180 ([M+H-propene]$^+$, 60)

EXAMPLE 64

Synthesis of 2-amino-6-chloro-4-ethoxypteridine

A suspension of the compound of example 62 (460 mg, 2.22 mmoles) in acetyl chloride (5.5 ml) was stirred at −40° C. Trifluoroacetic acid (1.69 ml) was then added dropwise. The resulting solution was slowly warmed up to 0° C. and stirred for an additional 4 hours at 0° C. Reaction was carefully quenched with ice, followed by neutralization with a concentrated ammonia solution (pH=8). The aqueous phase was extracted with $CH_2Cl_2$ (five times). The combined organic layers were concentrated in vacuo and the residue was purified by flash chromatography (silica, using a $CH_3OH/CH_2Cl_2$ mixture (1:99) as the eluent), thus providing the title compound as a yellow powder (360 mg, yield: 72%). This compound was further characterized as follows:
mass spectrum: m/z (%): 226 ([M+H]$^+$, 100),
$^1$H-NMR (200 MHz, DMSO-$d_6$): δ 1.42 (3H, t), 4.52 (2H, q), 7.42 (2H, d) and 8.85 (1H, s) ppm,
$^{13}$C-NMR (50 MHz, DMSO-$d_6$): δ 14.19, 63.58, 121.74, 140.22, 150.99, 156.13, 161.98 and 165.97 ppm.

EXAMPLE 65

Synthesis of 2-amino-6-chloro-4-isopropoxypteridine

The procedure as described in example 64 was followed, however starting from the compound of example 63. The mass spectrum data of the resulting compound are as follows: m/z (%): 240 ([M+H]$^+$, 55), 198 ([M+H-propene]$^+$, 100).

EXAMPLES 66 TO 83

Synthesis of 2-amino-6-aryl-4-ethoxypteridines and 2-amino-6-heteroaryl-4-ethoxypteridines The general procedure used for preparing 2-amino-6-aryl-4-ethoxypteridines is as follows: to a degassed solution of the compound of example 64 (50 mg, 0.22 mmole) in THF (5 ml) was added a degassed solution of sodium carbonate (5 ml of a 0.4 M solution in water), tetrakis(triphenylphosphine) palladium (0.013 mmole, 14 mg) and an arylboronic or (examples 72 and 73) heteroarylboronic acid (0.22 mmole). The solution was refluxed for 4 hours. Solvents were concentrated in vacuo and the residue was purified by flash chromatography (silica) with an appropriate $CH_3OH/CH_2Cl_2$ mixture (2:98 or 3:97) as the eluent (except for the compound of example 82, which was eluted with an acetone/$CH_2Cl_2$ (7:3) mixture). This procedure provided, with a yield ranging from 16% to 60% depending upon the aryl or heteroaryl group (from the arylboronic or heteroarylboronic acid) introduced at the 6-position of the pteridine ring, the following pure final compounds which were characterized by their mass spectrum MS and optionally by their $^1$H-NMR (200 MHz, DMSO-$d_6$) spectrum:

2-amino-6-(p-methoxyphenyl)-4-ethoxy-pteridine (example 66): MS 298 ([M+H]$^+$, 100), 270 ([M+H-ethene]$^+$, 55);

2-amino-6-(o-methoxyphenyl)-4-ethoxy-pteridine (example 67): MS 298 ([M+H]$^+$, 100), 270 ([M+H-ethene]$^+$, 30);

2-amino-6-(m-methoxyphenyl)-4-ethoxy-pteridine (example 68): MS 298 ([M+H]$^+$, 100), 270 ([M+H-ethene]$^+$, 35); $^1$H-NMR: 1.46 (3H, t), 3.85 (3H, s), 4.58 (2H, q), 7.06 (1H, dd), 7.33 (2H, br s), 7.46 (1H, t), 7.68 (1H, m) and 9.43 (1H, s) ppm;

2-amino-6-(3,4-difluorophenyl)-4-ethoxy-pteridine (example 69): MS 304 ([M+H]$^+$, 100), 270 ([M+H-ethene]$^+$, 35); $^1$H-NMR: 1.45 (3H, t), 4.57 (2H, q), 7.42 (2H, br s), 7.60 (1H, q), 7.98 (1H, d), 8.16 (1H, t) and 9.42 (1H, s) ppm;

2-amino-6-(p-dimethylaminophenyl)-4-ethoxy-pteridine (example 70): MS 311 ([M+H]$^+$, 100), 283 ([M+H-ethene]$^+$, 35);

2-amino-6-(p-trifluoromethylphenyl)-4-ethoxy-pteridine (example 71): MS 336 ([M+H]$^+$, 100), 308 ([M+H-ethene]$^+$, 50);

2-amino-6-(2-thienyl)-4-ethoxy-pteridine (example 72): MS 274 ([M+H]$^+$, 100), 246 ([M+H-ethene]$^+$, 40);

2-amino-6-(3-thienyl)-4-ethoxy-pteridine (example 73): MS 274 ([M+H]$^+$, 100), 246 ([M+H-ethene]$^+$, 45);

2-amino-6-(3,4-dichlorophenyl)-4-ethoxy-pteridine (example 74): MS 337 ([M+H]$^+$, 100); $^1$H-NMR: 1.46 (3H, t), 4.59 (2H, q), 7.42 (2H, br s), 7.81 (1H, d), 8.14 (1H, dd), 8.37 (1H, d) and 9.47 (1H, s) ppm;

2-amino-6-(p-cyanophenyl)-4-ethoxy-pteridine (example 75): MS 293 ([M+H]$^+$, 100), 265 ([M+H-ethene]+, 65);

2-amino-6-(p-ethoxyphenyl)-4-ethoxy-pteridine (example 76): MS 312 ([M+H]$^+$, 100), 284 ([M+H-ethene]$^+$, 70);

2-amino-6-(p-fluorophenyl)-4-ethoxy-pteridine (example 77): MS 286 ([M+H]$^+$, 100), 258 ([M+H-ethene]$^+$, 45);

2-amino-6-(p-ethylphenyl)-4-ethoxy-pteridine (example 78): MS 296 ([M+H]$^+$, 100), 268 ([M+H-ethene]$^+$, 45);

2-amino-6-(p-acetylphenyl)-4-ethoxy-pteridine (example 79): MS 310 ([M+H]$^+$, 100), 282 ([M+H-ethene]$^+$, 60);

2-amino-6-(3-methyl-4-fluorophenyl)-4-ethoxy-pteridine (example 80): MS 300 ([M+H]+, 100), 272 ([M+H-ethene]+, 30);

2-amino-6-(p-thiomethylphenyl)-4-ethoxy-pteridine (example 81): MS 314 ([M+H]+, 100), 286 ([M+H-ethene]+, 35);

2-amino-6-(p-N,N-dimethylbenzamido)-4-ethoxy-pteridine (example 82) MS 338 ([M+H]+, 100), 311 ([M+H-ethene]+, 15); and 2-amino-6-(3,4-dimethoxyphenyl)-4-ethoxy-pteridine (example 83): MS 328 ([M+H]+, 100), 300 ([M+H-ethene]+, 40).

EXAMPLES 84 TO 98

Synthesis of 2-amino-6-aryl-4-isopropoxypteridines and 2-amino-6-heteroaryl-4-isopropoxypteridines The procedure as described in examples 66–83 was followed while using 2-amino-6-chloro-4-isopropoxypteridine as the starting material, except that longer reaction times were needed (refluxing overnight instead of 4 hours). This procedure provided, with a yield ranging from 10% to 70% depending upon the aryl or heteroaryl group introduced at the 6-position of the pteridine ring, the following pure final compounds which were characterized by their mass spectrum:

2-amino-6-(3-methyl-4-methoxyphenyl)-4-isopropoxypteridine (example 84): MS 326 ([M+H]+, 100), 284 ([M+H-propene]+, 30);

2-amino-6-(3,4-dimethylphenyl)-4-isopropoxypteridine (example 85): MS 310 ([M+H]+, 100), 268 ([M+H-propene]+, 60);

2-amino-6-(3-chloro-4-trifluoromethylphenyl)-4-isopropoxypteridine (example 86): MS 384 ([M+H]+, 20), 342 ([M+H-propene]+, 50);

2-amino-6-(3-chloro-4-fluorophenyl)-4-isopropoxypteridine (example 87): MS 334 ([M+H]+, 20), 292 ([M+H-propene]+, 50);

2-amino-6-(p-N,N-diethylbenzamido)-4-isopropoxypteridine (example 88): MS 381 ([M+H]+, 100);

2-amino-6-(p-trifluoromethylphenyl)-4-isopropoxypteridine (example 89): MS 350 ([M+H]+, 100), 308 ([M+H-propene]+, 30);

2-amino-6-(3,4-difluorophenyl)-4-isopropoxypteridine (example 90): MS 318 ([M+H]+, 100), 276 ([M+H-propene]+, 50);

2-amino-6-(p-methoxyphenyl)-4-isopropoxypteridine (example 91): MS 312 ([M+H]+, 100), 270 ([M+H-propene]+, 50);

2-amino-6-(p-ethoxyphenyl)-4-isopropoxypteridine (example 92): MS 326 ([M+H]+, 55), 284 ([M+H-propene]+, 100);

2-amino-6-(p-dimethylbenzamido)-4-isopropoxypteridine (example 93): MS 353 ([M+H]+, 75), 311 ([M+H-propene]+, 100);

2-amino-6-(3-thienyl)-4-isopropoxypteridine (example 94): MS 288 ([M+H]+, 55), 246 ([M+H-propene]+, 100);

2-amino-6-(p-cyanophenyl)-4-isopropoxypteridine (example 95): MS 307 ([M+H]+, 40), 265 ([M+H-propene]+, 100);

2-amino-6-(p-benzoic acid methyl ester)-4-isopropoxypteridine (example 96): MS 340 ([M+H]+, 75), 298 ([M+H-propene]+, 100);

2-amino-6-(p-acetylphenyl)-4-isopropoxypteridine (example 97): MS 324 ([M+H]+, 55), 282 ([M+H-propene]+, 100); and 2-amino-6-(3,4-dimethoxyphenyl)-4-isopropoxypteridine (example 98): MS 342 ([M+H]+, 100), 300 ([M+H-propene]+, 60).

EXAMPLE 99

Synthesis of 2,6-diamino-5-nitroso-4-hydroxypyrimidine

To a solution of 2,6-diamino-4-hydroxypyrimidine (12.9 g, 102.2 mmoles) in 200 ml of a 10% acetic acid solution in water at 80° C. was added dropwise a solution of NaNO$_2$ (7.05 g, 102.2 mmoles) in 20 ml water. A pink precipitate was formed, which was further stirred for 1 hour at 80° C. The reaction mixture was cooled down in the refrigerator overnight. The precipitate was filtered off and dried over P$_2$O$_5$, providing the title compound as a pink powder (15.43 g, yield: 97%). The spectral data are in accordance with literature data (Landauer et al. in *J. Chem. Soc.* (1953) 3721–3722).

EXAMPLE 100

Synthesis of 2,5,6-triamino-4-hydroxyprimidine

A suspension of the compound of example 99 (15 g, 96.7 mmoles) in an ammonium sulfide solution (20% in water, 200 ml) was stirred overnight at 50° C. The reaction mixture was cooled down in the refrigerator and the precipitate was filtered off, providing the title compound as a yellow powder (11.33 g, yield: 83%). The spectral data are identical with literature data (Landauer et al. cited supra).

EXAMPLE 101

Synthesis of 2-amino-6-(3,4-dimethoxyphenyl)pterine

To a boiling solution of the compound of example 100 (2.4 g, 17 mmoles) in methanol (100 ml, with 0.9 N HCl) was added dropwise a solution of 3,4-dimethoxyphenylglyoxal mono-oxime (3.8 g, 18 mmoles) in methanol (100 ml). The reaction mixture was heated under reflux for 4 hours. The precipitate formed was filtered off, washed with water, then ethanol and diethyl ether, and dried over P$_2$O$_5$ under vacuum, providing the title compound as a yellow powder (4.33 g, yield: 85%). This compound was further characterized by the following spectra:

$^1$H-NMR (500 MHz, TFA): δ 4.11 (3H, s), 4.07 (3H, s), 7.21 (1H, d), 7.78 (1H, dd), 7.81 (1H, d) and 9.32 (1H, s) ppm;

$^{13}$C-NMR (125 MHz, TFA): δ 56.39, 56.7, 111.94, 113.21, 123.22, 127.41, 127.91, 145.92, 149.39, 150.46, 152.47, 153.15, 155.13 and 161.59 ppm.

Example 102

Synthesis of 2-acetylamino-6-(3,4-dimethoxyphenyl)pterine

A suspension of the compound of example 101 (10.46 g, 35 mmoles) in acetic anhydride (600 ml) and acetic acid (200 ml) was refluxed for 1 hour until a clear solution was formed. By cooling down the reaction mixture in the refrigerator, the precipitate formed was filtered off, washed with ethyl acetate and diethyl ether, and then dried over $P_2O_5$ under vacuum, providing the title compound as a yellow powder (9.19 g, yield: 77%). This compound was further characterized by the following spectra:

MS: m/z (%): 300 ([M+H]$^+$, 100);

$^1$H-NMR (200 MHz, DMSO-d$_6$): δ 2.22 (3H, s), 3.84 (3H, s), 3.87 (3H, s), 7.14 (1H, d), 7.75 (2H, m) and 9.51 (1H, s) ppm.

EXAMPLE 103

Synthesis of 2-acetylamino-4-(1,2,4-triazolyl)-6-(3, 4-dimethoxyphenyl)pteridine To a solution of phosphorus oxychloride (1.68 ml, 18 mmoles) and 1,2,4-triazole (4.96 g, 72 mmoles) in dry pyridine (110 ml) was added the compound of example 102 (2.45 g, 7.18 mmoles). The suspension was stirred at room temperature for 4 hours. The precipitate was filtered off, washed with pyridine, toluene and diethyl ether. The resulting solid was dried over $P_2O_5$ under vacuum, providing the title compound as a yellow powder (2 g, yield: 80%) which afforded the following mass spectrum: 392 ([M+H]$^+$, 100).

EXAMPLES 104 AND 105

Synthesis of 2-amino-4-mercaptoethyl-6-(3,4-dimethoxyphenyl)pteridine and 2-amino-4-mercaptoisopropyl-6-(3,4-dimethoxyphenyl)pteridine To a suspension of the compound of example 103 (0.25 mmole, 100 mg) in dioxane (5 ml) was added 1 mmole of either ethanethiol (example 104) or isopropanethiol (example 105) and sodium (12 mg, 0.5 mmole). The suspension was stirred for 24 hours at room temperature. The solvent was concentrated in vacuo and the residue purified by flash chromatography (silica, using a $CH_3OH/CH_2Cl_2$ mixture (5:95) as an eluent), followed by purification by preparative TLC, providing the pure title compounds as yellow powders with yields ranging from 20 to 30%. Both compounds were characterized by their mass spectrum as follows:

2-amino-4-mercaptoethyl-6-(3,4-dimethoxyphenyl) pteridine: 344 ([M+H]$^+$, 100);

2-amino-4-mercaptoisopropyl-6-(3,4-dimethoxyphenyl) pteridine: 357 ([M+H]$^+$, 100).

EXAMPLE 106

Synthesis of a Mixture of 2,4-diamino-6-(p-methoxyphenyl) pteridine and 2,4-diamino-7-(P-methoxyphenyl)pteridine 2,4,5,6-tetra-aminopyrimidine (10 mmoles, 1.4 g) was dissolved in water (50 ml) and the pH was adjusted to 9 with ammonium hydroxide. A solution of 4-methoxyphenylglyoxal (11 mmoles, 1.8 g) in ethanol (10 ml) was added dropwise and the solution was refluxed for 1 hour. The yellow precipitate formed was filtered off and washed with water, ethanol and diethyl ether. NMR analysis reveals the obtention of a mixture (1.2 g, 45% yield) consisting of 87% of 2,4-diamino-7-(p-methoxyphenyl)pteridine and 13% of 2,4-diamino-7-(p-methoxy-phenyl)pteridine.

$^1$H-NMR (500 MHz, TFA): δ 4.04 (3H, s), 4.08 (3H, s), 7.15 (2H, d), 7.25 (2H, d), 8.19 (2H, d), 8.30 (2H, d), 9.27 (1H, s) and 9.37 (1H, s) ppm.

EXAMPLE 107

Synthesis of a Mixture of 2-amino-6-(p-methoxyphenyl)pterin and 2-amino-7-(p-methoxyphenyl) pterin The mixture obtained in example 106 (1.2 g, 4.5 mmoles) was suspended in NaOH 1 N (80 ml) and refluxed till a solution was obtained. The hot solution was treated with acetic acid till pH 5, then cooled down and the resulting precipitate was filtered off and washed with water, ethanol and diethyl ether, providing a mixture of 2-amino-6-(p-methoxyphenyl)pterin and 2-amino-7-(p-methoxyphenyl) pterin as a yellow powder (1 g, yield: 82%). Mass spectrum: 270 ([M+H]$^+$, 100).

EXAMPLE 108

Synthesis of 2-acetylamino-6-(p-methoxyphenyl) pterin and 2-acetylamino-7-(p-methoxyphenyl) pterin A suspension of the mixture obtained in example 107 (7.43 mmoles, 2 g) was suspended in a mixture of acetic anhydride (50 ml) and acetic acid (50 ml). The suspension was refluxed for 4 hours till a clear solution was obtained. Some insoluble material was filtered off and the solution was partly evaporated till precipation starts. Further precipitation was achieved overnight in the refrigerator. The resulting precipitate was filtered off and washed with ethyl acetate and diethyl ether, providing a mixture of 2-acetylamino-6-(pmethoxyphenyl)pterin and 2-acetylamino-7-(p-methoxyphenyl)pterin as a yellow powder (2.1 g, 91% yield). Mass spectrum: 312 ([M+H]$^+$, 100).

EXAMPLE 109

Synthesis of 2-acetylamino-4-(1,2,4-triazolyl)-6-(p-methoxyPhenyl) pteridine and 2-acetylamino-4-(1,2, 4-triazolyl)-7-(p-methoxyphenyl) Pteridine To a suspension of the mixture obtained in example 108 (1.5 g, 4 mmoles) in dry pyridine (100 ml) was added 1,2,4-triazole (830 mg, 12 mmoles) and 4-chlorophenyl phosphorodichloridate (1 ml, 6 mmoles). The suspension was stirred for 2 days at room temperature under nitrogen. The solvents were removed in vacuo. The solid material was suspended in dichloromethane and washed with 2% HCl. Evaporation of the solvents provided a mixture of 2-acetylamino-4-(1,2,4-triazolyl)-6-(p-methoxyphenyl) pteridine and 2-acetylamino-4-(1,2,4-triazolyl)-7-(p-methoxyphenyl) pteridine.

EXAMPLE 110

Synthesis of 2-amino-4-isopropoxy-7-(p-methoxyphenyl) Pteridine

To a suspension of the mixture obtained in example 109 (180 mg, 0.50 mmole) in isopropanol (8 ml) was added sodium (23 mg, 1 mmole). The suspension was stirred at room temperature overnight. The solvents were evaporated and the residue was purified by preparative TLC (silica, using a methanol/$CH_2Cl_2$ (7:93) mixture as the eluent). At this stage, both regioisomers obtained were separated, thus providing the pure title compound as a yellow powder (yield: 45%) which was further characterized by its mass spectrum: 312 ([M+H]$^+$, 65), 270 ([M+H-propene]$^+$, 100).

EXAMPLE 111

Synthesis of 2-amino-4-isopropoxy-7-(3,4-dimethoxyphenyl) Pteridine

The sequence of reactions described in examples 106 to 110 was followed, however starting from 3,4-dimethoxyphenylglyoxal instead of 4-methoxyphenylglyoxal in the first step. This provided 2-amino-4-isopropoxy-7-(3,4-dimethoxyphenyl) pteridine, a compound which was further characterized by its mass spectrum: 342 ([M+H]$^+$, 55), 300 ([M+H-propene]$^+$, 75).

EXAMPLE 112

Synthesis of 2-amino-4-ethoxy-7-(3,4-dimethoxyphenyl) Pteridine

The sequence of reactions described in examples 106 to 110 was followed, however starting from 3,4-dimethoxyphenylglyoxal instead of 4-methoxyphenylglyoxal in the first step, and from ethanol instead if isopropanol in the last step. This provided 2-amino-4-ethoxy-7-(3,4-dimethoxyphenyl) pteridine, a compound which was further characterized as follows:

MS: 328 ([M+H]$^+$, 100), 300 ([M+H-ethene]$^+$, 40);
$^1$H-NMR (500 MHz, DMSO-d$_6$): δ 1.44 (3H, t), 3.86 (3H, s), 3.88 (3H, s), 4.54 (2H, q), 7.13 (1H, d), 7.16 (2H, br s), 7.85 (1H, d), 7.88 (1H, dd) and 9.06 (1H, s) ppm;
$^{13}$C-NMR (125 MHz, DMSO-d$_6$): δ 14.25, 55.67, 55.76, 63.06, 110.39, 111.89, 121.13, 121.25, 128.24, 136.87, 149.28, 151.62, 155.82, 156.72, 162.03 and 166.70 ppm.

EXAMPLE 113

Synthesis of 2-amino-4-methoxy-7-(3,4-dimethoxyphenyl) Pteridine

The sequence of reactions described in examples 106 to 110 was followed, however starting from 3,4-dimethoxyphenylglyoxal instead of 4-methoxyphenylglyoxal in the first step, and from methanol instead if isopropanol in the last step. This provided 2-amino-4-ethoxy-7-(3,4-dimethoxyphenyl) pteridine, a compound which was further characterized by its mass spectrum: 314 ([M+H]$^+$, 100), 300 ([M+H-methane]$^+$, 20).

EXAMPLE 114

Lymphocyte Activation Tests

Pteridine derivatives were first dissolved (10 mM) in dimethylsulfoxide (hereinafter referred as DMSO) and further diluted in culture medium before use for the following in vitro experiments. The commercially available culture medium consisted of RPMI-1640+10% foetal calf serum (FCS). Some pteridine derivatives described the previous examples were tested in the following lymphocyte activation tests:

Mixed Lymphocyte Reaction

Peripheral blood mononuclear cells (hereinafter referred as PBMC) were isolated from heparinized peripheral blood by density gradient centrifugation over Lymphoprep (Nycomed, Maorstua, Norway). Allogeneic PBMC or Eppstein-Barr Virus-transformed human B cells [commercially available under the trade name RPM11788 (ATCC name CCL156)] which strongly express B7-1 and B7-2 antigens were used as stimulator cells after irradiation with 30 Gy. MLR was performed in triplicate wells. After 5 days incubation at 37° C., 1 μCi [$^3$H]-thymidine was added to each cup. After a further 16 hours incubation, cells were harvested and counted in a β-counter. Inhibition of proliferation by a compound (drug) described in some of the previous examples was counted using the formula:

$$\% \text{ inhibition} = \frac{(cpm + \text{drugs}) - (cpm \text{ cult. med})}{(cpm - \text{drugs}) - (OD \text{ cult. med})} \times 100$$

wherein cpm is the thymidine count per minute. The MLR assay is regarded by those skilled in the art as an in vitro analogue of the transplant rejection since it is based on the recognition of allogeneic major histocompatibility antigens on the stimulator leukocytes, by responding lymphocytes.

Assays for CD3 and CD 28

T cells were purified by removing non-T cells. Briefly, monocytes were removed by cold agglutination. The resulting lymphoid cells were further purified by a cell enrichment immunocolumn [Cellect Human T commercially available from Biotex, Edmonton, Alberta, Canada)] by a process of negative selection. More than 95% of the B cells were removed with this procedure. After depletion, the resulting T cell preparation was highly purified, i.e. these cells could not be activated by phytohaemagglutinin (PHA) or rIL-2 alone at concentrations capable of stimulating RBMC prior to deletion.

Highly purified T cells (10$^6$/ml) were stimulated by immobilized anti-CD3 or anti-CD28 monoclonal antibodies (hereinafter referred as mAb) in the presence of phorbol myristate acetate (hereinafter referred as PMA). Anti-CD3 mAb (available from CLB, Amsterdam, Netherlands) were fixed on a 96 microwell plates by incubating the wells with 50 μl of mAb solution (⅟800 dilution in culture medium). For anti-CD28 mAb (available from CLB, Amsterdam, Netherlands) 50 μl (⅟650 dilution in culture medium) was added directly to the wells. Further, a 20 μl PMA (commercially available from Sigma, St. Louis, Mo., USA) solution (final concentration: 0.5 ng/ml) was added. Subsequently, 20 μl of a pteridine derivative described in the previous examples were added by serial dilution in triplicate wells. Finally 100 μl of the T-cell suspension (106/ml) was added. After 48-hour incubation at 37° C. in 5% CO$_2$, 20 μl of a bromo-deuridine (hereinafter referred as BrdU) 100 μM solution (commercially available as Cell Proliferation Elisa from Boehringer-Mannheim Belgium) was added to each well. After a further overnight incubation, T-cell proliferation was measured using a colorimetric immunoassay for qualification of cell proliferation based on the incorporation of BrdU during DNA synthesis. Optical density (hereinafter referred as OD) was measured by a Behring EL311 plate reader at 450 nm (reference wavelength: 690 nm). Inhibition of proliferation by the pteridine derivative (drug) was counted while using the formula:

$$\% \text{ inhibition} = \frac{(OD + \text{drugs}) - (OD \text{ cult. med})}{(OD - \text{drugs}) - (OD \text{ cult. med})} \times 100$$

Table 1 (wherein ND means not determined) below shows the IC$_{50}$ values for various pteridine derivatives in the MLR test and in the CD3 and CD28 assays. The IC$_{50}$ value represents the lowest concentration of the pteridine derivative (expressed in μmole/l) that resulted in a 50% suppression of the MLR or a 50% reduction in T-cell proliferation (for the CD3 and CD28 assay).

TABLE 1

| Example n° | MLR | CD3 | CD28 |
|---|---|---|---|
| 1 | 15 | 110 | 80 |
| 2 | 12 | 4.0 | 12 |
| 3 | 25 | 160 | 100 |
| 4 | >200 | 140 | 110 |
| 5 | 140 | >200 | >200 |
| 6 | 5.0 | 15 | 15 |
| 7 | 3.6 | 4.5 | 3.9 |
| 8 | 12 | 7.5 | 7.5 |
| 9 | 15 | 80 | 20 |
| 10 | 17 | 50 | 20 |
| 11 | 12 | 20 | 20 |
| 12 | 0.08 | 0.5 | 0.1 |
| 13 | 75 | 25 | 25 |
| 14 | 100 | 75 | 20 |
| 15 | 50 | 20 | 15 |
| 16 | 3.5 | 4.3 | 3.2 |
| 17 | 15 | 25 | 25 |
| 18 | 13 | 9.7 | 6.7 |
| 19 | 8.5 | 5.7 | 2.8 |
| 20 | 2.2 | 0.8 | 0.7 |
| 21 | 15 | 100 | 20 |
| 22 | 12 | 20 | 20 |
| 23 | 15 | 125 | 20 |
| 24 | 0.1 | 0.4 | 0.3 |
| 25 | 15 | 80 | 20 |
| 26 | 15 | 70 | 25 |
| 27 | 4.6 | 14 | 12 |
| 28 | 0.4 | 0.5 | 0.4 |
| 29 | 15 | 40 | 25 |
| 30 | 4.8 | 11 | 4.2 |
| 31 | 12.3 | 11.7 | 4.2 |
| 32 | 2.0 | 7.3 | 6.5 |
| 33 | 22 | 17 | 3.7 |
| 34 | 12 | 11.7 | 5.0 |
| 35 | 2.0 | 20 | 15 |
| 36 | 10.5 | 14 | 4.5 |
| 37 | 2.8 | 14.8 | 4.5 |
| 38 | ++ | ++ | ++ |
| 39 | ++ | + | + |
| 40 | ++ | ++ | ++ |
| 41 | 0 | + | + |
| 42 | +++ | ++ | ++ |
| 43 | ++ | ++ | ++ |
| 44 | ++ | + | + |
| 45 | 0 | + | + |
| 46 | ++ | ++ | + |
| 47 | +++ | ++ | ++ |
| 48 | + | + | + |
| 49 | ++ | ++ | ++ |
| 50 | ++ | + | + |
| 51 | +++ | ND | ND |
| 52 | ++ | + | + |
| 53 | ND | +++ | +++ |
| 68 | 8.3 | 20 | 7.0 |
| 69 | >10 | 9.0 | 4.0 |
| 71 | 10 | 10 | 0.8 |
| 73 | ND | 15 | 0.7 |
| 78 | 8.2 | 10 | 10 |

TABLE 1-continued

| Example n° | MLR | CD3 | CD28 |
|---|---|---|---|
| 83 | 0.9 | 0.7 | 0.7 |
| 85 | 10 | ND | ND |
| 98 | 0.4 | 6.7 | 1.7 |

0 stands for concentrations of at least 151 μM,
+ stands for concentrations 16–150 μM,
++ stands for concentrations 1–15 μM, and
+++ stands for concentrations lower than 1 μM.

The above data show that, whereas known immunosuppressant drugs like CyA are known to be active only in the CD3 assay, the pteridine derivatives according to the present invention were also active in the CD28 assay which is Ca$^{2+}$-calmodulin resistant. The CD28 pathway is a so-called cosignal pathway which is important for inducing energy and even tolerance in T-cells.

EXAMPLE 115

TNF-α and IL-1 β Assays

Peripheral blood mononuclear cells (herein referred as PBMC), in response to stimulation by lipopolysaccharide (LPS), a gram-negative bacterial endotoxin, produce various chemokines, in particular human TNF-α and IL-1 β. Inhibition of the activation of PBMC can therefore be measured by the level of suppression of the production of TNF-α or IL-1 β by PBMC in response to stimulation by LPS.

Such inhibition measurement was performed as follows: PBMC were isolated from heparinized peripheral blood by density gradient centrifugation over Lymphoprep (commercially available from Nycomed, Norway). LPS was then added to the PMBC suspension in complete medium (10$^6$ cells/ml) at a final concentration of 1 μg/ml. The pteridine derivative to be tested was added at different concentrations (0.1 μM, 1 μM and 10 μM) and the cells were incubated at 37° C. for 72 hours in 5% CO$_2$. The supernatants were collected, then TNF-α and/or IL-1 β concentrations were measured with respectively an anti-TNF-a antibody or an anti-IL-1 β antibody in a sandwich ELISA (Duo Set ELISA human TNFα, commercially available from R&D Systems, United Kingdom). The colorimetric reading of the ELISA was measured by a Multiskan RC plate reader (commercially available from ThermoLabsystems, Finland) at 450 nm (reference wavelength: 690 nm). Data analysis was performed with Ascent software 2.6. (also from ThermolLabsystems, Finland): a standard curve (recombinant human TNFα) was drawn and the amount (pg/ml) of each sample on the standard curve was determined.

The % suppression of human TNFα production or human IL-1 β by the pteridine derivatives of the invention (drugs) was calculated using the formula:

$$\% \text{ suppression} = \frac{\text{pg/ml in drugs} - \text{pg/ml in cult. med.}}{(\text{pg/ml in cult. med.} + LPS) - \text{pg/ml cult. med.}}$$

Table 2 below shows the IC$_{50}$ values (expressed in μM) of the tested pteridine derivatives in the TNF-α assay.

TABLE 2

| Example n° | TNF-α |
|---|---|
| 59 | 8.0 |
| 63 | 4.0 |
| 65 | 9.1 |
| 66 | 4.5 |
| 67 | 10.0 |
| 68 | 10.0 |
| 72 | 8.5 |
| 77 | 8.1 |
| 78 | 8.5 |
| 80 | 6.8 |
| 81 | 10.0 |
| 83 | 6.6 |
| 85 | 6.7 |
| 87 | 7.5 |
| 89 | 9.1 |
| 90 | 6.6 |
| 91 | 6.2 |
| 92 | 10.0 |
| 94 | 7.6 |
| 95 | 6.3 |
| 97 | 9.1 |
| 98 | 3.5 |

EXAMPLE 116

Inhibition of the Release of Cytokines Involved in Asthma

The pteridine derivative of example 24 was tested, according to experimental procedures well established in the art, in the inhibition of two cytokines, IL-5 and IL-10, known to be involved in the development of asthma and other forms of severe allergic conditions. At the concentration of 0.1 µM/l, i.e. the $IC_{50}$ value of this derivative in the MLR test, the said derivative inhibited the release of IL-5 and IL-10 by 70% and 39%, respectively.

EXAMPLE 117

Inhibition of the Metastasis of Melanoma Cells in Mice

C57BL/6 mice were injected with $1.5 \times 10^6$ B16BL/6 melanoma cells and were divided into 2 groups. Five days after the injection of the tumor cells, the two groups of animals were administered intraperitoneously, three times a week for two subsequent weeks, either (treated group) 20 mg/kg of the pteridine derivative of example 24 or (control group) the vehicle (5% DMSO in phosphate buffered saline). At the end of the experiment, all surviving tumor-bearing mice were sacrificed and examined in order to assess the absence or presence of the black metastases in inguinal and/or para-aortic lymph nodes (macroscopic metastasis). The findings were confirmed by histology, and the experiment done twice. The pooled results of the two experiments show that 80% of animals from the control group had metastases whereas only 33% of animals from the treated group had metastases.

EXAMPLE 118

In Vivo Leukocyte Activation and Immunosuppression Whole Blood Assay

In response to non-self antigens (e.g. microbial antigens, allo-antigens, altered self antigens and auto-antigens), immune cells such as lymphocytes, NK cells, monocytes/macrophages and dentritic cells are activated to generate antigen-reactive effector cells. Activated immune cells up-regulate a number of pro-inflammatory genes encoding cytokines (e.g. IL-2, IFN-γ, and TNF-α), chemokines (e.g. monocyte chemo-attractant protein-1 (MCP-1), macrophage inflammatory protein-i (MIP-1) and RANTES), and cell surface molecules. These leukocyte surface molecules may include activation associated molecules (e.g. CD69, the lymphocyte early activation molecule, and CD71, the transferin receptor), adhesion molecules (e.g. ICAM-1, LFA-1 and L-selectins), co-stimulatory molecules (e.g. CD28, B7-1 and CD40L) and receptors for cytokines and chemokines (e.g. IL-2R and CCR1).

Immunomodulatory therapies are active by interfering with the responses of the immune system. Reliable, easy, fast and quantitative methods for monitoring the evolution of the leucocyte surface and cytoplasma phenotypes during activation are critical in evaluating the functional competence of the immune cells (e.g., during HIV infection), as well as the efficacy of immunoregulatory therapies in order to achieve optimal therapeutic effects and minimal side effects. Moreover, examination of drug action on leukocyte activation is able to provide critical evaluation of pharmacokinetic and pharmacodynamic effects of immunomodulatory agents. Within this context, the following provides a useful in vivo leukocyte activation and immunosuppression whole blood assay (hereinafter referred as WBA).

Inbred mice (e.g. AKR strain), weighting from 20 to 30 g, were stimulated by intra-peritoneal injection with mitogens specific for T cells (e.g. Concanavalin A, hereinafter referred as ConA, 500 µg per mouse), B cells or monocytes/macrophages (e.g. LPS 20 µg per mouse). The pteridine derivatives of example 83 and, respectively, example 98, were administered intraperitoneously (30 mg/kg per day, administered 2 hours before ConA injection). Peripheral blood was collected 24, 36, 48, and respectively 72 hours after stimulation for immune fluorescence staining and FACScan analysis.

FACScan analysis proceeded as follows: heparinized whole blood (50 µl) was removed of red blood cells by incubation with a lysing buffer. The remaining leukocytes were double-stained with phycoerythrin-conjugated antibodies specific for T cells (e.g. T cell receptor TCR), B cells (e.g. CD45R/B220 (commercially available from Pharmingen) or monocytes/macrophages (e.g. F4/80) (commercially available from Serotec) in combination with FITC-conjugated antibodies against various cell surface markers such as CD69 (early activation molecule), CD25 (IL-2 receptor), CD71 (transferring receptor), B7-1/2 (ligand for the co-stimulatory molecule CD28) and CD11b (complement receptor 3). Cells were examined by flow cytometry using CellQuest software (commercially available from Decton Dickinson).

Peripheral blood T cells expressed an up-regulated level of CD69, representing up to 3% of $TCR^+,CD69^+$ cells respectively 1 and 2 days following ConA injection, as compared to baseline levels (0.5%). T cells from mice treated with the pteridine derivatives of examples 83 and 98 show a remarkable reduction of this response to 1.6% and 2.4% respectively.

Peripheral blood T cells showed a rapid up-regulation of CD71 from baseline level (4.8%) to 9.3% and 5.5% after 1 day and 2 days, respectively. The pteridine derivatives of examples 83 and 98 suppressed ConA-stimulated CD71 up-regulation on T cells to baseline levels.

Peripheral blood T cells expressed increased levels of IL-2R with up to 3% of TCR+, IL-2R+cells 1 and 2 days following ConA stimulation, with peak levels after day 2. Administration of the pteridine derivatives of examples 83 and 98 effectively suppresses this effect by reducing expression to 1.5% and 1.7%, respectively.

Up to 6.6% of peripheral blood T cells displayed an up-regulation of the CD134 molecule expression within 2 days following ConA stimulation, i.e. a twofold increase of baseline levels (2.2%). Treatment with the pteridine derivatives of examples 83 and 98 suppressed this response to 3.5% and 4.2%, respectively.

This FACScan-based cell surface phenotype analysis for in vivo leukocyte activation, namely for an in vivo whole blood assay, demonstrates the immunosuppressive effects of the pteridine derivatives of examples 83 and 98 in vivo. This observation is consistent with the above experimental results in vitro showing that both compounds inhibit T cell activation and proliferation in mixed lymphocyte culture, and in the CD3 and CD28 assays.

In vivo WBA by injecting immune activators, followed by FACS analysis of leukocyte surface phenotypes in the whole blood can be applied to monitor in vivo activation of different types of leukocytes such as T cells, B cells, monocytes/macrophages, and dentritic cells. This technology allows simple, rapid, direct, stable and quantitative evaluation of the immune competence of the said leukocytes, as well as pharmacokinetic and pharmacodynamic profiles of the pteridine derivatives used as immunomodulatory agents in vivo.

Despite various in vitro models are used for the discovery of new immunosuppressive drugs, there are essentially no ideal animal models that are simple, fast, and cost-effective. Models of organ transplantation (e.g. hearts, kidney and skin) in rodents are limited by technical difficulty, and cannot be used for primary screening of a large numbers of candidate drugs. Although recently a mouse model of drug-mediated immunosuppression based on rejection of an allogeneic subcutaneous tumor was reported, several significant limitations should be considered. For example first, the host immune responses against this specific tumor seems to be T cell-dependent, and thus the activity of a drug on other cell types such as B cells, monocytes/macrophages and dentritic cells cannot be evaluated by using this model. Secondly, immunosuppressive drugs with anti-proliferation activity (e.g. rapamycin) may play a direct role on tumor angiogenesis and tumor cell growth. Thirdly, the feature of chronic rejection of the tumor (e.g. after 14 days) prevents from evaluating the pharmacodynamic properties of drugs. Finally, this animal tumor rejection model is inaccurate (e.g. quantified by size measurement) and time-costly (at least 14 days).

FACScan-based in vitro WBA has been used to investigate the pharmacodynamic effects of immunomodulatory drugs administered in vivo, but only by taking blood from treated recipients and stimulating their lymphocytes in vitro. These methods show remarkable advantages as compared to the purified peripheral blood mononuclear cell (PBMC) cultures in terms of maintaining cell viability, as well as the effects within the whole blood of immunomodulatory drugs previously administered in vivo. However, in vitro WBA has important flaws. First, the evaluation of the drug effects uses an in vitro activation system, including manipulation, dilution and stimulation of the blood, and subsequent culture of the blood in the presence of an exogenous serum (e.g. foetal calf serum). This in vitro activation system may not necessarily and accurately reflect the effects of drugs on leukocyte activation in vivo, nor does this assay give information on the absorption or metabolite production of drugs that may occur in vivo. Secondly, in vitro stimulation of the whole blood by mitogens (e.g. Con A, PHA or LPS) causes aggregation of activated leukocytes, platelets and red blood cells, as well as generation of spontaneous fluorescence by in vitro damaged cells. These alterations frequently interfere with the FACS analysis. Thirdly, plastic adhesion of monocytes/macrophages during in vitro culture may induce additional steps in order to examine these cell types. Finally, in vitro culture of leucocytes is expensive, time consuming, and poorly reproducible. The above described in vivo WBA assay is able to overcome the above mentioned problems and may be characterized as follows:

- leukocyte stimulation is performed in vivo (e.g. by in vivo injection of leucocyte stimulating agents such as, but not limited to, ConA or LPS, thus enabling the full in vivo evaluation of the effect of drugs on leucocyte activation in physiological conditions,
- various stimuli can be used that are specific for different cell types, including T cells (e.g. ConA, anti-CD3 antibodies and alloantigens), B cells (e.g. T cell-independent xeno-antigens, sheep red blood cells, TNP-ficoll, TNP-BA, anti-IgM antibodies and LPS) and monocytes/macrophages (e.g. LPS, TNF-α and IFN-γ). Given the time-dependent nature of the expression of cell surface antigens, the effects of drugs can be studied on early as well as on late leucocyte activation, e.g. by analyzing the expression of early (e.g. CD69 and CD71) or late (e.g. IL-2R and CD134) appearing antigens,
- by varying the time of administration of a drug prior to or after in vivo injection of the leucocyte stimuli, the pharmacodynamic profile of the said drug can be determined. Similarly, the effects and the duration of activity of a drug via different routes of administration, e.g. intraperitoneously, intramuscularly and orally, can be studied,
- by using the same test in immunodeficient animals (e.g. T cell-deficient nude mice), the effect of a drug on selected immune phenomena can be investigated (e.g. on in vivo T cell-independent B cell activation in nude mice; T cell activation in T cell-reconstituted SCID mice that have congenital defect on both T and B cells),
- peripheral leukocytes from different sources, such as spleen, lymph nodes and peritoneal cavity, can be tested,
- in combining FACScan-based intracellular phenotype analysis with e.g. intracellular cytokine staining, or DNA synthesis by BrdU or 5- and 6-carboxyfluorescein diacetate succinimidyl ester (CFSE) incorporation, or cell cycle studies, the information obtained can be further broadened, and
- the method is able to help in elucidating the mechanism underlying in vivo up-regulation of expression of certain activation molecules, such as CD69, CD25, CD71, CD134 and B7-1/2, in various types of peripheral blood leucocytes.

The invention claimed is:

1. A pteridine derivative selected from the group consisting of:
   2-amino-4-ethoxy-6-(4-methoxyphenyl)-pteridine
   2-amino-4-ethoxy-6-(2-methoxyphenyl)-pteridine
   2-amino-4-ethoxy-6-(3-methoxyphenyl)-pteridine
   2-amino-4-ethoxy-6-(3,4-difluorophenyl)-pteridine
   2-amino-4-ethoxy-6-(4-dimethylaminophenyl)-pteridine
   2-amino-4-ethoxy-6-(4-trifluoromethylphenyl)-pteridine 2-amino-4-ethoxy-6-(2-thienyl)-pteridine
2-amino-4-ethoxy-6-(3-thienyl)-pteridine
2-amino-4-ethoxy-6-(3,4-dichlorophenyl)-pteridine
2-amino-4-ethoxy-6-(4-cyanophenyl)-pteridine
2-amino-4-ethoxy-6-(4-ethoxyphenyl)-pteridine
2-amino-4-ethoxy-6-(4-fluorophenyl)-pteridine
2-amino-4-ethoxy-6-(4-ethylphenyl)-pteridine
2-amino-4-ethoxy-6-(4-acetylphenyl)-pteridine
2-amino-4-ethoxy-6-(3-fluoro-4-methylphenyl)-pteridine
2-amino-4-ethoxy-6-(4-thiomethylphenyl)-pteridine
2-amino-4-ethoxy-6-(4-N,N-dimethylbenzamido)-pteridine
2-amino-4-isopropoxy-6-(3-methyl-4-methoxyphenyl)-pteridine
2-amino-4-isopropoxy-6-(3,4-dimethylphenyl)-pteridine
2-amino-4-isopropoxy-6-(3-chloro-4-trifluoromethylphenyl)-pteridine
2-amino-4-isopropoxy-6-(3-chlorol-4-fluorophenyl)-pteridine
2-amino-4-isopropoxy-6-(4-N,N-diethylbenzamido)-pteridine
2-amino-4-isopropoxy-6-(4-trifluoromethylphenyl)-pteridine
2-amino-4-isopropoxy-6-(3,4-difluorophenyl)-pteridine
2-amino-4-isopropoxy-6-(4-methoxyphenyl)-pteridine
2-amino-4-isopropoxy-6-(4-ethoxyphenyl)-pteridine
2-amino-4-isopropoxy-6-(4-N,N-dimethylbenzamido)-pteridine
2-amino-4-isopropoxy-6-(3-thienyl)-pteridine
2-amino-4-isopropoxy-6-(4-cyanophenyl)-pteridine
2-amino-4-isopropoxy-6-(4-benzoic acid methyl ester)-pteridine
2-amino-4-isopropoxy-6-(4-acetylphenyl)-pteridine
2-amino-4-isopropoxy-6-(3,4-dimethoxyphenyl)-pteridine
2-amino-4-ethylthio-6-(3,4-dimethoxyphenyl)-pteridine, and
2-amino-4-isopropylthio-6-(3,4-dimethoxyphenyl)-pteridine.

2. A pharmaceutical composition comprising as an active principle at least one pteridine derivative according to claim 1.

* * * * *

UNITED STATES PATENT AND TRADEMARK OFFICE
CERTIFICATE OF CORRECTION

| | |
|---|---|
| PATENT NO. | : 7,276,506 B2 |
| APPLICATION NO. | : 10/651604 |
| DATED | : October 2, 2007 |
| INVENTOR(S) | : Mark Jozef Albert Waer et al. |

It is certified that error appears in the above-identified patent and that said Letters Patent is hereby corrected as shown below:

Column 1,
       Line 20, replace "cells" with --cell--.
       Line 30, replace "cells" with --cell--.

Column 3,
       Line 24, replace "organ The" with --organ. The--.
       Line 39, replace "4-1 BB" with --4-1BB--.

Column 15, Line 52, replace "monoor" with --mono- or--.

Column 16,
       Line 15, replace "mtoluyl," with --m-totuyl,--.
       Line 44, replace "symetrically" with --symmetrically--.

Column 17,
       Line 58, replace "$R_x$," with --$R_1$,--.
       Line 63, replace ""aryl alkylaryl"," with --"aryl," "alkylaryl,"--.

Column 18, Line 9, replace "0C," with --OC,--.

Column 19, Line 63, replace "choride" with --chloride--.

Column 20,
       Line 15, replace "II" with --11--.
       Line 35, replace "$R_x$" with --$R_1$--.
       Line 41, replace "tetraminopyrimidine," with --tetraaminopyrimidine--.
       Line 55, replace "nucleophie" with --nucleophile--.
       Line 58, replace "$R_x$" with --$R_1$--.

Column 22, Line 9, replace "$C_{14}$ alkyloxycarbonyl," with --$C_{1-4}$ alkyloxycarbonyl--.

Column 28, Line 34, replace "equiment" with --equipment--.

Column 29, Line 5, replace "deivative" with --derivative--.

UNITED STATES PATENT AND TRADEMARK OFFICE
CERTIFICATE OF CORRECTION

PATENT NO. : 7,276,506 B2
APPLICATION NO. : 10/651604
DATED : October 2, 2007
INVENTOR(S) : Mark Jozef Albert Waer et al.

It is certified that error appears in the above-identified patent and that said Letters Patent is hereby corrected as shown below:

Column 31, Line 52, replace "NEM+1%" with --NEAA+1%--.

Column 32,
    Line 37, replace "pyridine," with --avridine--.
    Line 64, replace "beween" with --between--.

Column 33,
    Line 36, replace "intraperiteneously)" with --intraperitoneously)--.
    Line 45, replace "spondilytis," with --spondylitis,--.

Column 34,
    Line 26, replace "lymp node tumor," with --lymph node tumor,--.
    Line 40, replace "graminae," with --gramineae,--.

Column 35,
    Line 52, replace "alcanolamine" with --alkanolamine--.
    Line 62, replace "dipalmitoylphoshatidylcholine" with
        --dipalmitoylphosphatidylcholine--.

Column 36,
    Line 8, replace "poylypropylene" with --polypropylene--.

Column 39,
    Line 36, replace "2-amino-4-alkylamino6-arylpteridines," with
        --2-amino-4-alkylamino-6-arylpteridines,--.
    Line 58, replace "2,6-diamino4-(N-containing" with
        --2-amino-4-(N-containing--.

Column 43, Line 10, replace "2-amino-4-ethoxypteridine-N-oxide" with
        --2-amino-4-ethoxypteridine-$N^8$-oxide--.

UNITED STATES PATENT AND TRADEMARK OFFICE
CERTIFICATE OF CORRECTION

PATENT NO. : 7,276,506 B2
APPLICATION NO. : 10/651604
DATED : October 2, 2007
INVENTOR(S) : Mark Jozef Albert Waer et al.

It is certified that error appears in the above-identified patent and that said Letters Patent is hereby corrected as shown below:

Column 48,
    Line 28, replace "precipation" with --precipitation--.
    Line 31, replace "2-acetylamino-6-(pmethoxyphenyl)pterin" with
        --2-acetylamino-6-(p-methoxyphenyl)pterin--.
    Line 38, replace "2-acetylamino-4-(1,2,4-triazolyl)-6-(p-methoxyPhenyl)"
        with --2-acetylamino-4-(1,2,4-triazolyl)- 6-(p-methoxy-phenyl)--.

Column 50,
    Line 7, replace "RPM11748" with --RPMI1748--.
    Line 56, replace "(106/ml)" with --($10^6$/ml)--.

Column 51, Line 11, replace "$1C_{50}$" with --$IC_{50}$--.

Column 52, Line 45, replace "anti-TNF-a" with --anti-TNF-α--.

Column 54, Line 7, replace "protein-i" with --protein-1--.

Signed and Sealed this

Eleventh Day of August, 2009

David J. Kappos
*Director of the United States Patent and Trademark Office*